US008029793B2

(12) United States Patent
Yoshida et al.

(10) Patent No.: US 8,029,793 B2
(45) Date of Patent: Oct. 4, 2011

(54) METHODS FOR INHIBITING CELL PROLIFERATION

(75) Inventors: Akira Yoshida, Kanagawa (JP); Syunsuke Yanoma, Kanagawa (JP); Fumikazu Hirose, Kanagawa (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 604 days.

(21) Appl. No.: 10/258,477

(22) PCT Filed: Apr. 26, 2001

(86) PCT No.: PCT/JP01/03665
§ 371 (c)(1), (2), (4) Date: Mar. 3, 2003

(87) PCT Pub. No.: WO01/82968
PCT Pub. Date: Nov. 8, 2001

(65) Prior Publication Data
US 2004/0001824 A1  Jan. 1, 2004

(30) Foreign Application Priority Data

Apr. 28, 2000  (JP) ................................ 2000-131793
Jun. 9, 2000  (JP) ................................ 2000-173834

(51) Int. Cl.
*C07K 16/18* (2006.01)
*A61K 38/29* (2006.01)

(52) U.S. Cl. .................................................. 424/143.1

(58) Field of Classification Search ................ 424/143.1
See application file for complete search history.

(56) References Cited

U.S. PATENT DOCUMENTS

| 4,771,124 | A |  | 9/1988 | Rosenblatt et al. ............ 530/324 |
| 5,001,223 | A |  | 3/1991 | Rosenblatt et al. ............ 530/324 |
| 5,217,896 | A |  | 6/1993 | Kramer et al. ............ 435/240.27 |
| 5,626,845 | A |  | 5/1997 | Yoneda et al. .............. 424/145.1 |
| 5,849,695 | A |  | 12/1998 | Cohen et al. ..................... 514/12 |
| 5,993,817 | A |  | 11/1999 | Yoneda et al. .............. 424/158.1 |
| 6,903,194 | B1 | * | 6/2005 | Sato et al. ................... 530/387.1 |
| 2005/0244414 | A1 | * | 11/2005 | Mundy et al. .............. 424/145.1 |

FOREIGN PATENT DOCUMENTS

| EP | 0 293 130 |  | 11/1988 |
| EP | 0 293 158 |  | 11/1988 |
| EP | 0 449 405 |  | 10/1991 |
| EP | 0 811 383 |  | 12/1997 |
| EP | 0 878 201 | A1 | 11/1998 |
| EP | 0 962 467 | A1 | 12/1999 |
| EP | 1 004 313 | A1 | 5/2000 |
| EP | 1 090 643 | A1 | 4/2001 |
| EP | 0 813 423 | B1 | 7/2002 |
| JP | 2-207099 |  | 8/1990 |
| JP | 4-502408 |  | 5/1992 |
| JP | 04228089 | A | 8/1992 |
| JP | 7-165790 |  | 6/1995 |
| JP | 7-316195 |  | 12/1995 |
| JP | 11-80025 |  | 3/1999 |
| JP | 11-222440 |  | 8/1999 |
| JP | 2000-080100 |  | 3/2000 |
| WO | WO 89/11297 |  | 11/1989 |
| WO | WO 89/11298 |  | 11/1989 |
| WO | WO 90/07861 |  | 7/1990 |
| WO | WO 91/16928 |  | 11/1991 |
| WO | WO 92/00753 |  | 1/1992 |
| WO | WO 92/17602 |  | 10/1992 |
| WO | WO 92/19759 |  | 11/1992 |
| WO | WO 93/13133 |  | 7/1993 |
| WO | WO 94/11523 |  | 5/1994 |
| WO | WO 96/03437 |  | 2/1996 |
| WO | WO 96/39184 |  | 2/1996 |
| WO | WO 96/22790 |  | 8/1996 |
| WO | WO 96/26737 |  | 9/1996 |
| WO | WO 96/33735 |  | 10/1996 |
| WO | WO 98/13388 |  | 4/1998 |
| WO | WO 98/51329 |  | 11/1998 |
| WO | WO 99/57139 |  | 11/1999 |
| WO | WO 00/00219 |  | 1/2000 |

OTHER PUBLICATIONS

Nakashima et al (J. Pathol. 175:227-236 (1995)).*
Guise et al. (J. Clin. Invest. 98(7):1544-1549 (1996)).*
Cataisson et al. (J. Bone & Mineral Res. 15:2129-2139 (Nov. 11, 2000).*
Kaiser, S.M., et al., (1992) J. Biol. Chem.; 267(19):13623-13628.*
Fortier, A.H., et al., (1999) Journal of the National Cancer Institute; 91:1635-1640.*
McGowan, E.M., et al., (1999) Molecular Endocrinology; 13:1657-1671.*
Reichert et al. Nature Biotech. 23(9): 1073-1078 (2005).*
Mayo Clinic.com "Monoclonal antibody drugs" pp. 1-5 (Jan. 2007).*
Sato et al. Sem. Oncol. 30(5):167-73 (2003) (Abstract).*
Onuma et al. (Anticancer Res. 24(5A): 2665-73 (2004) (Abstract).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
http//en.wikipedia.org/wiki/Monoclonal antibody therapy, pp. 1-6 (Aug. 3, 2009).*
Fujimori et al. (J. Nuc. Med. 31:1191-1198 (1990)).*
Beckman et al. (Can. 109:170-179 (2007).*
Thurber et al. (Adv. Drug Deliv. Rev. 60:1421-1434 (2008).*
Rudnick et al. (Can. Biotherp. & Radiopharm. 24: 155-162 (2009)).*
Funk et al., 1999, "Expression of parathyroid hormone-related protein and the parathyroid hormone/parathyroid hormone-related protein receptor in rat thymic epithelial cells," J. Anat., 194(2): 255-264.
Philbrick et al., 1996, "Defining the Roles of Parathyroid Hormone-Related Protein in Normal Physiology," Physiological Reviews, 76(1): 127-173.
Sato et al., 1993, "Passive Immunization with Anti-Parathyroid Hormone-Related Protein Monoclonal Antibody Markedly Prolongs Survival Time of Hypercalcemic Nude Mice Bearing Transplanted Human PTHrP-Producing Tumors," J. Bone Miner. Res., 8(7): 849-860.

(Continued)

Primary Examiner — Lynn Bristol
(74) Attorney, Agent, or Firm — Oblon, Spivak, McClelland, Maier & Neustadt, L.L.P.

(57) ABSTRACT

Provided are proliferation inhibitors for cells whose proliferation is stimulated by PTHrP (34-53), comprising a substance inhibiting the binding of PTHrP (1-34) to its receptor.

5 Claims, 3 Drawing Sheets

OTHER PUBLICATIONS

International Search Report for PCT/JP01/03665, mailed Aug. 14, 2001.
U.S. Appl. No. 09/269,332, filed Mar. 25, 1999, Sato et al.
U.S. Appl. No. 10/337,981, filed Nov. 12, 1999, Sato et al.
U.S. Appl. No. 09/720,326, filed Dec. 22, 2000, Sato et al.
U.S. Appl. No. 10/019,501, filed Dec. 31, 2001, Ogata et al.
U.S. Appl. No. 10/019,571, filed Dec. 31, 2001, Ogata et al.
U.S. Appl. No. 10/019,785, filed Jan. 4, 2002, Saito et al.
U.S. Appl. No. 10/169,003, filed Jun. 26, 2002, Yamazaki et al.
U.S. Appl. No. 10/182,018, filed Jul. 24, 2002, Kato et al.
U.S. Appl. No. 10/229,149, filed Aug. 27, 2002, Saito et al.
Abou-Samra et al., Expression Cloning of a Common Receptor for Parathyroid Hormone and Parathyroid Hormone-Related Peptide from Rat Osteoblast-Like Cells: A Single Receptor Stimulates Intracellular Accumulation of Both cAMP and Inositol Trisphosphates and Increases Intracellular Free Calcium, *Proceedings of the National Academy of Sciences*, 89:2732-2736 (1992).
Baba, PTH/PTHrP, *Clinical Calcium*, 5:97-101 (1995) (English Translation).
Beck et al., Lipolytic Factors Associated with Murine and Human Cancer Cachexia, *Journal of the National Cancer Institute*, 82:1922-1926 (1990).
Belyavsky et al., PCR-Based cDNA Library Construction: General cDNA Libraries at the Level of a Few Cells, *Nucleic Acids Research*, 17:2919-2933 (1989).
Burtis, Parathyroid Hormone-Related Protein: Structure, Function, and Measurement, *Clinical Chemistry*, 38:2171-2183 (1992).
Carter et al., Humanization of an Anti-p185$^{HER2}$ Antibody for Human Cancer Therapy, *Proceedings of the National Academy of Sciences*, 89:4285-4289 (1992).
Chirgwin et al., Isolation of Biologically Active Ribonucleic Acid From Sources Enriched in Ribonuclease, *Biochemistry*, 18:5294-5299 (1979).
Chomczynski et al., Single-Step Method of RNA Isolation by Acid Guanidinium Thiocyanate-Phenol-Chloroform Extraction, *Analytical Biochemistry*, 162:156-159 (1987).
Chothia, Canonical Structures for the Hypervariable Regions of Immunoglobulins, *Journal of Molecular Biology*, 196:901-917 (1987).
Co et al., Chimeric and Humanized Antibodies with Specificity for the CD33 Antigen, *The Journal of Immunology*, 148:1149-1154 (1992).
Co et al., Humanized Antibodies for Antiviral Therapy, *Proceedings of the National Academy of Sciences*, 88:2869-2873 (1991).
Coleman et al., Biochemical Mechanisms of Parathyroid Hormone Action, *The Parathyroids, Basic and Clinical Concepts*, 239-258 (1994).
Cuisinier et al., Mechanisms That Generate Human Immunoglobulin Diversity Operate From the 8$^{th}$ Week of Gestation in Fetal Liver, *European Journal of Immunology*, 23:110-118 (1993).
Dariavach et al., Human Immunoglobulin C$_\lambda$6 Gene Encodes the Kern $^+$Oz λ Chain and C$_\lambda$4 and C$_\lambda$5 are Pseudogenes, *Proceedings of the National Academy of Sciences*, 84:9074-9078 (1987).
Deftos et al., Utilization of a Potentially Universal Downstream Primer in the Rapid Identification and Characterization of Vλ Genes From Two New Human Vλ Families, *Scandinavian Journal of Immunology*, 39:95-103 (1994).
de St. Groth et al., Production of Monoclonal Antibodies: Strategy and Tactics, *Journal of Immunological Methods*, 35:1-21 (1980).
Dworkin et al., Dietary Intake in Patients with Acquired Immunodeficiency Syndrome (AIDS), Patients with AIDS-Related Complex, and Serologically Positive Human Immunodeficiency Virus Patients: Correlations with Nutritional Status, *Journal of Parenteral and Enteral Nutrition*, 14:605-609 (1990).
Farmer et al., Speculations on the Design of Nonpeptidic Peptidomimetics, *TIPS*, 4:362-365, (1982).
Frohman et al., Rapid Production of Full-Length cDNAs From Rare Transcripts: Amplification Using a Single Gene-Specific Oligonucleotide Primer, *Proceedings of the National Academy of Sciences*, 85:8998-9002 (1988).
Galfrè et al., Rat x Rat Hybrid Myelomas and a Monoclonal Anti-Fd Portion of Mouse IgG, *Nature*, 277:131-133 (1979).
Gorman et al., Reshaping a Therapeutic CD4 Antibody, *Proceedings of the National Academy of Sciences*, 88:4181-4185 (1991).
Hammond et al., Respiratory Muscle Strength in Congestive Heart Failure, *Chest*, 98:1091-1094 (1990).
Hardman et al., Goodman & Gilman's, The Pharmacological Basis of Therapeutics, *Hormones and Hormone Anatgonists*, McGraw-Hill Co. (USA) 9$^{th}$ ed., pp. 1528-1529 (1995).
Hardman et al., Goodman & Gilman's The Pharmacological Basis of Therapeutics, *Hormones and Hormone Anatgonists*, McGraw-Hill Co. (USA) 9$^{th}$ ed., pp. 1523-1524 (1995).
Hardman et al., Goodman & Gilman's The Pharmacological Basis of Therapeutics, McGraw-Hill Co. (USA) 8$^{th}$ ed., pp. 3-32 (1990).
Harris et al., Therapeutic Antibodies, The Coming of Age, *TIBTECH*, 11:42-44 (1993).
Hosoi et al., PTH, PTHrP, and CGRP in Hypertension Research, *Nippon Rinshou*, 55(8):1950-1957 (1997) (English Abstract).
Ikeda, Molecular Biology of Parathyroid Hormone-Related Peptide, *Nihon Rinshou*, 53:37-45 (1995) (English Abstract).
Ikeda, Development of Novel Endocrinotherapy Targeting Cancer and Paraneoplastic Syndromes, *Progress in Clinical Pharmacology*, 16:155-161 (1995) (English Abstract).
Jones et al., Rapid PCR-Cloning of Full-Length Mouse Immunoglobulin Variable Regions, *Bio/Technology*, 9:88-89 (1991).
Jüppner et al., A G Protein-Linked Receptor for Parathyroid Hormone and Parathyroid Hormone-Related Peptide, *Science*, 254:1024-1026 (1991).
Kaji et al., Role of Dual Signal Transduction Systems in the Stimulation of Bone Resorption by Parathyroid Hormone-Related Peptide, The Direct Involvement of cAMP-Dependent Protein Kinase, *Horm. Metab. Res.*, 25:421-424 (1993).
Kajimura et al., Toxohormones Responsible for Cancer Cachexia Syndrome in Nude Mice Bearing Human Cancer Cell Lines, *Cancer Chemother Pharmacol*, 38:S48-S52 (1996).
Karlsson et al., Kinetic Analysis of Monoclonal Antibody-Antigen Interactions with a New Biosensor Based Analytical System, *Journal of Immunological Methods*, 145:229-240 (1991).
Kato et al., Incisor Change Induced by Excessive PTHrP in Rats, Abstracts of 16$^{th}$ Meeting of Japanese Society of Toxicologic Pathology, p. 17 (2000) (English Translation).
Kearney et al., A New Mouse Myeloma Cell Line That Has Lost Immunoglobulin Expression But Permits the Construction of Antibody-Secreting Hybrid Cell Lines, *The Journal of Immunology*, 123:1548-1550 (1979).
Kemp et al., Parathyroid Hormone-Related Protein of Malignancy: Active Synthetic Fragments, *Science*, 238:1568-1570 (1987).
Kettleborough et al., Humanization of a Mouse Monoclonal Antibody by CDR-Grafting: The Importance of Framework Residues on Loop Conformation, *Protein Engineering*, 4:773-738 (1991).
Köhler et al., Derivation of Specific Antibody-Producing Tissue Culture and Tumor Lines by Cell Fusion, *European Journal of Immunology*, 6:511-519 (1976).
Kohno et al., Synovial Fluids from Patients with Osteoarthritis and Rheumatoid Arthritis Contain High Levels of Parathyroid Hormone-Related Peptide, *Journal of Bone and Mineral Research*, 2(5): 847-854 (1997).
Kozak, At Least Six Nucleotides Preceding the AUG Initiator Condon Enhance Translation in Mammalian Cells, *Journal of Molecular Biology*, 196:947-950 (1987).
Kukreja et al., Tumor Resection and Antibodies to Parathyroid Hormone-Related Protein Cause Similar Changes on Bone Histomorphometry in Hypercalcemia of Cancer, *Endocrinology*, 127(1):305-310 (1990).
Kukreja et al., Antibodies to Parathyroid Hormone-Related Protein Lower Serum Calcium in Athymic Mouse Models of Malignancy-Associated Hypercalcemia Due to Human Tumors, *The Journal of Clinical Investigation*, 82:1798-1802 (1988).
Liu et al., Developmental Role of PHTrP in Murine Molars, *European Journal Oral Sciences*, 106 (suppl 1):143-146 (1998).
LoBuglio et al., Mouse/Human Chimeric Monoclonal Antibody in Man; Kinetics and Immune Response, *Proceedings of the National Academy of Sciences*, 86:4220-4224 (1989).

Lundgren et al., Parathyroid Hormone (1-34) Receptor-Binding and Second-Messenger Response in Rat Incisor Odontoblasts, *Calcif. Tissue Int.*, 62:255-259 (1998).

Maeda et al., Targeted Overexpression of Parathyroid Hormone-Related Protein (PTHrP) to Vascular Smooth Muscle in Transgenic Mice Lowers Blood Pressure and Alters Vascular Contractility, *Endocrinology*, 140(5) (1999).

Maeda et al., Construction of Reshaped Human Antibodies with HIV-Neutralizing Activity, *Human Antibodies and Hybridomas*, 2:124-134 (1991).

Margulies et al., Somatic Cell Hybridization of Mouse Myeloma Cells, *Cell*, 8:405-415 (1976).

Marosi et al., Fatal Encephalitis in a Patient with Chronic Graft-Versus Host Disease, *Bone Marrow Transplantation*, 6:53-57 (1990).

Mizuno et al., Regulation of the Vasomotor Activity of Lymph Microvessels by Nitric Oxide and Prostaglandins, *American Journal of Physiology*, 274, pp. R790-R796 (1998).

Mizuno et al., Parathyroid Hormone-Related Protein-(1-34) Inhibits Intrinsic Pump Activity of Isolated Murine Lymph Vessels, *American Journal Physiology, Heart Circulation Physiology*, 281, pp. H60-H66 (2001).

Mizushima et al., pEFBOS, A Powerful Mammalian Expression Vector, *Nucleic Acids Research*, 18:5322 (1990).

Morimoto, PTH/PTHrP, *Clinical Calcium*, 5(12):50-54 (1995) (English Translation).

Moseley et al., Parathyroid Hormone-Related Protein Purified from a Human Lung Cancer Cell Line, *Proceedings of the National Academy of Sciences*, 84:5048-5052 (1987).

Mountain et al., Engineering Antibodies for Therapy, *Biotechnol Genet Eng Rev.*, 10:1-142 (1992).

Muller et al., Uberwachung und Handhabung von Zentrainervosen und Intestinalen System zur Behandlung der Tumorkachexie, *Langenbecks Arch Chir Suppl. II*, pp. 261-265 (1990) (English Abstract).

Mulligan et al., Synthesis of Rabbit β-globin in Cultured Monkey Kidney Cells Following Infection with a SV40 β-globin Recombinant Genome, *Nature*, 277:108-114 (1979).

Natsume et al., Binding Assay and Analysis of Kinetic Parameters by BIAcore Biosensor, *Experimental Medicine*, 13:85-91 (1995) (English Translation).

Ogata, Parathyroid Hormone-Related Protein as a Potential Target of Therapy for Cancer-Associated Morbidity, *Cancer*, 88:2902-2911 (2000).

Ohtomo et al., Humanization of Mouse ONS-M21 Antibody with the Aid of Hybrid Variable Regions, *Molecular Immunology*, 32:407-416 (1995).

Olstad et al., Expression and Characterization of a Recombinant Human Parathyroid Partial Agonist with Antagonistic Properties: Gly-hPTH(-1→+84), *Peptides*, 16:1031-1037 (1995).

Palmieri et al., Muscle Calcium Accumulation in Muscular Dystrophy, Intracell. Calcium Regul., Proc. Int. Symp., pp. 335-347 (1986).

Philbrick et al., Parathyroid Hormone-Related Protein is Required for Tooth Eruption, *Proceedings of the National Academy of Sciences*, 95:11846-11851 (1998).

Queen et al., A Humanized Antibody that Binds to the Interleukin 2 Receptor, *Proceedings of the National Academy of Sciences*, 86:10029-10033 (1989).

Riechmann et al., Reshaping Human Antibodies for Therapy, *Nature*, 332:323-327 (1988).

Roe et al., A Photometric Method for the Determination of Insulin in Plasma and Urine, *Journal of Biological Chemistry*, 173:839-845 (1949).

Rosen et al., The Effect of PTH Antagonist BIM-44002 on Serum Calcium and PTH Levels in Hypercalcemic Hyperparathyroid Patients, *Calcified Tissue international*, 61:455-459 (1997).

Roubini et al., Synthesis of Fully Active Biotinylated Analogues of Parathyroid Hormone and Parathyroid Hormone-Related Protein as Tools for the Characterization of Parathyroid Hormone Receptors, *Biochemistry*, 31:4026-4033 (1992).

Sato et al., Reshaping a Human Antibody to Inhibit the Interleukin 6-dependent Tumor Cell Growth, *Cancer Research*, 53:851-856 (1993).

Sato et al., A Highly Sensitive Bioassay for PTH Using ROS 17/2.8 Subclonal Cells, *Acta Endocrinologica*, 116:113-120 (1987).

Sato, Malignancy-associated Hypercalcemia: Pathogenesis and Treatment, *Journal of Tokyo Women's Medical College*, 58(9):939-946 (1988) (English Abstract).

Saito et al., Potential Involvement of PHTrP in Cancer Cachexia, *Japanese Journal of Cancer Research*, 90 (Suppl.): Abstract No. 2195 (1999) (English Abstract).

Shigeno, PTH/PTHrP Receptor, *Clinical Calcium*, 5(3):79-83 (1995) (English Translation).

Shulman et al., A Better Cell Line for Making Hybridomas Secreting Specific Antibodies, *Nature*, 276:269-270 (1978).

Stewart et al., Clinical Review 16: Parathyroid Hormone-Related Proteins: Coming of Age in the 1990s, *Journal of Clinical Endocrinology and Metabolism*, 71:1410-1414 (1990).

Strewler, The Physiology of Parathyroid Hormone-Related Protein, *The New England Journal of Medicine*, 342(3):177-185 (2000).

Sumiya et al., Hypercalcemia with Malignant Tumor, *Saishin Igaku*, 46(2):315-324 (1991) (English Abstract).

Sutliff et al., Vasorelaxant Properties of Parathyroid Hormone-Related Protein in the Mouse: Evidence for Endothelium Involvement Independent of Nitric Oxide Formation, *Endocrinology*, 140(5):2077-2083 (1999).

Suva et al., A Parathyroid Hormone-Related Protein Implicated in Malignant Hypercalcemia: Cloning and Expression, *Science*, 237:893-896 (1987).

Takahashi et al., Structure of Human Immunoglobulin Gamma Genes: Implications for Evolution of a Gene Family, *Cell*, 29:671-679 (1982).

Takahashi et al., Concentrations of Blood Parathyroid Hormone Related Protein (PTHrP) and Various Cytokines in Malignant Tumor Patients, *Record of the Japan Society of Clinical Biochemistry and Metabolism*, 35:107 (1998) (English Abstract).

Tanaka, Triple Paraneoplastic Syndrome of Hypercalcemia, Leukocytosis and Cachexia in Two Human Tumor Xerografts in Nude Mice, *Japanese Journal of Clinical Oncology*, 26:88-94 (1996).

Tempest et al., Reshaping a Human Monoclonal Antibody to Inhibit Human Respirtaory Syncytial Virus Infection in vivo, *Bio/Technology*, 9:266-271 (1991).

Tenorio et al., An Immunohistochemical Investigation of the Expression of Parathyroid Hormone Receptors in Rat Cementoblasts, *Archs Oral Biol.*, 41:299-305 (1996).

Tisdale et al., Cancer Cachexia, *International Journal of Pancreatology*, 7:141-150 (1990).

Trowbridge, Interspecies Spleen-Myeloma Hybrid Producing Monoclonal Antibodies Against Mouse Lymphocyte Surface Glycoprotein, T200, *Journal of Experimental Medicine*, 148:313-323 (1978).

Verhoeyen et al., Reshaping Human Antibodies; Grafting an Antilysozyme Activity, *Science*, 239:1534-1536 (1988).

Weissglas et al., Hypercalcemia and Cosecretion of Interleukin-6 and Parathyroid Hormone Related Peptide by a Human Renal Cell Carcinoma Implanted into Nude Mice, *The Journal of Urology*, 153:854-857 (1995).

Wong et al., Modulation of Antibody Affinity by an Engineered Amino Acid Substitution, *Journal of Immunology*, 154(7):3351-8 (1995).

Yamamoto et al., Parathyroid Hormone-Related Peptide-(1-34) PTHrP-(134) Induces Vasopressin Release from the Rat Supraoptic Nucleus in Vitro through a Novel Receptor Distinct from a Type I or Type II PTH/PTHrP Receptor, *Endocrinology*, 138(5):2066-2072 (1997).

Yelton et al., Fusion of Mouse Myeloma and Spleen Cells, Lymphocyte Hybridomas, Second Workshop on "Functional Properties of Tumors of T and B Lymphocytes," Sponsored by the National Cancer Institute (NIH) 1-7 (1978).

Yoshida et al., Study of Abnormal Calcium Level in Myotonic Dystrophy-Part II: with Respect to Nephrogenous Cylic AMP and Immunoreactivity of Serum Parathyroid Hormone, *The Japanese Endocrine Society Endocrine Journal*, 64(7):539-547 (1988) (English Abstract).

Zylicz et al., Metabolic Response to Enteral Food in Different Phases of Cancer Cachexia in Rats, Oncology, 47:87-91 (1990).

García-Ocaña et al.,"Parathyroid Hormone-Related Protein Is an Autocrine Modulator of Rabbit Proximal Tubule Cell Growth," *Journal of Bone and Mineral Research* 10(12):1875-1884 (1995).

García-Ocaña et al., "Expression and Role of Parathyroid Hormone-Related Protein in Human Renal Proximal Tubule Cells During Recovery from ATP Depletion," *Journal of the American Society of Nephrology* 10(2):238-244 (1999).

Hastings et al., "Parathyroid Hormone-Related Protein, an Autocrine Growth Inhibitor of Alveolar Type II Cells," *The American Journal of Physiology* 272(3):L394-L399 (1997).

Valín et al., "Antiproliferative Effect of the C-Terminal Fragments of Parathyroid Hormone-Related Protein, PTHrP-(107-111) and (107-139), on Osteoblastic Osteosarcoma Cells," *Journal of Cellular Physiology* 170(2):209-215 (1997).

European Search Report for EP 01 92 5993, Jun. 9, 2005.

Kong X F et al., 1994, "The rat, mouse and human genes encoding the receptor for parathyroid hormone and parathyroid hormone-related peptide are highly homologous," Biochemical and Biophysical Research Communications, 200(3):1290-1299.

Official Action in EP 01 925 993.6-1222 (May 29, 2006).

Office Action dated Feb. 22, 2007, for European Patent Application No. 01 925 993.6-1222.

Nowak, R.A., et al., "Transforming Growth Factor-β Stimulates Mouse Blastocyst Outgrowth Through a Mechanism Involving Parathyroid Hormone-Related Protein," Biol. Reprod., 60:85-93 (1999).

Paul, B. J. Burton, et al., "Parathyroid hormone-related peptide can regulate the growth of human lung cancer cells, and may form part of an autocrine TGF-æ loop", FEBS, vol. 305, No. 3, pp. 228-232, Jul. 1992.

Paul, B. J. Burton, et al.,"Parathyroid Hormone Related Peptide can Function as an Autocrine Growth Factor in Human Renal Cell Carcinoma", Biochemical and Biophysical Research Communications, vol. 167, No. 3, 1980, pp. 1134-1138.

Javier Benitez-Verguizas, et al., "Proliferative Effect of Parathyroid Hormone-Related Protein on the Hypercalcemic Walker 256 Carcinoma Cell Line", Biochemical and Biophysical Research Communications, vol. 198, No. 3, 1984, pp. 1281-1289.

Kyoji Ikeda, et al., "Transcriptional Regulation of the Parathyroid Hormone-related Peptide Gene by Glucocorticoids and Vitamin D in a Human C-cell Line", The Journal of Biological Chemistry, vol. 264, No. 27, Issue of Sep. 25, pp. 15743-15746, 1989.

A. P. B. Dackiw, et al. "Role of Parathyroid Hormone Related Protein (PTHRP) in Anaplastic Thyroid Cancer", Proceedings of the American Association for Cancer Research, vol. 41, Mar. 2000, XP-001536818, p. 206.

\* cited by examiner

Test of inhibiting cell proliferation (TTA-2, 48 hours)

Test of inhibiting cell proliferation (TTA-1, 48 hours)

Test of inhibiting cell proliferation (KTA-2, 48 hours)

METHODS FOR INHIBITING CELL PROLIFERATION

TECHNICAL FIELD

The present invention relates to a proliferation inhibitor for cells whose proliferation is stimulated by a parathyroid hormone-related peptide fragment.

BACKGROUND ART

A parathyroid hormone-related peptide (hereinafter, PTHrP) is a protein produced by a tumor, which is a major causative agent of humoral hypercalcemia of malignancy. A PTHrP induces humoral hypercalcemia of malignancy (hereinafter referred to as "HHM"), which is produced by tumor, by promoting bone resorption and renal reabsorption of calcium. Such an effect is known to be induced by a peptide site (referred to as PTHrP (1-34)) of the sequence of amino acids 1 to 34 on the N terminus of PTHrP through its receptor, a PTH/PTHrP receptor (J. Bone & Mine. Res. (1993) 8, 849-860). Currently, calcitonin and bisphosphonate preparations having an inhibitory action on bone resorption are used to treat HHM. However, since the progress of HHM is so rapid as to significantly deteriorate the QOL (Quality of Life) of patients with terminal cancer, development of a more effective therapeutic agent to respond to each cause has been awaited.

PTHrP has been suggested to have biological activity also at peptide sites other than PTHrP (1-34) (described in Naokazu NAGATA; Table 2 of CLINICAL CALCIUM, 5(3), 103-106, 1995). However, it has not yet been known that a peptide site (referred to as PTHrP (34-53)) corresponding to the sequence of amino acids 34 to 53 on the N terminal side of PTHrP produces an effect to stimulate cell proliferation.

DISCLOSURE OF THE INVENTION

Figure 1:
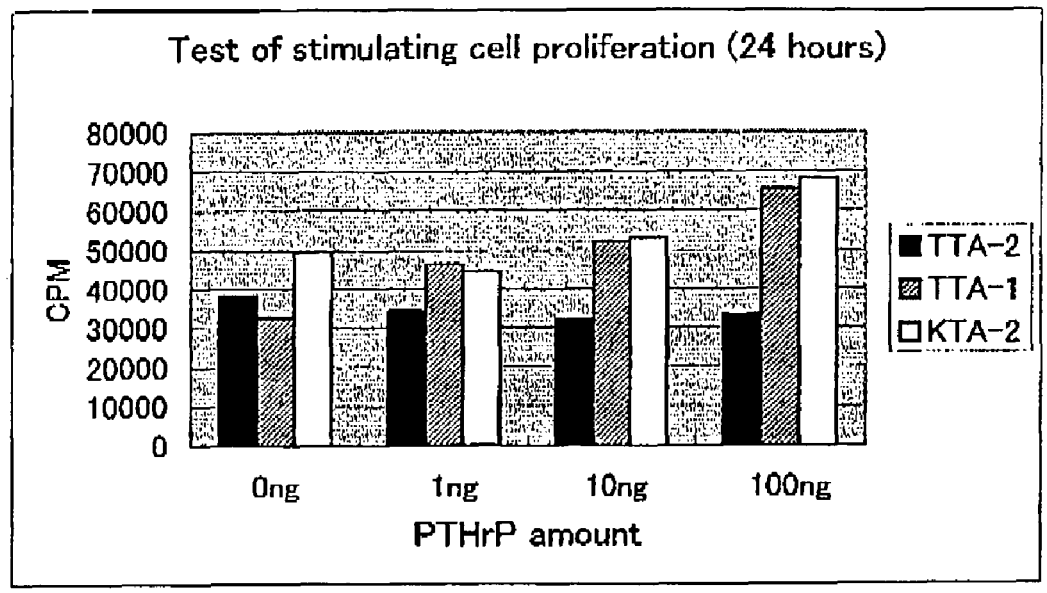
FIG. 1 shows the result of a test of stimulating cell proliferation with PTHrP. Briefly, anaplastic thyroid cell lines TTA-1 (hatched bars), TTA-2 (solid bars), and KTA-2 (unfilled bars) were seeded at $1 \times 10^4$ cells per well in a 96-well plate. Cells were incubated for two days in complete medium and then shifted to serum-free medium for day 3. Cells were treated with PTHrP (34-53) at 0, 1, 10, and 100 ng/mL and treated with trypsin 24 (top panel) and 48 (bottom panel) hours later. Cells were labeled with $^3$H-TdR for 6 hours (0.25 µCi/well) and incorporation of label was measured by liquid scintillation counting. Measurements were performed in triplicate and average results are presented.
Figure 1:
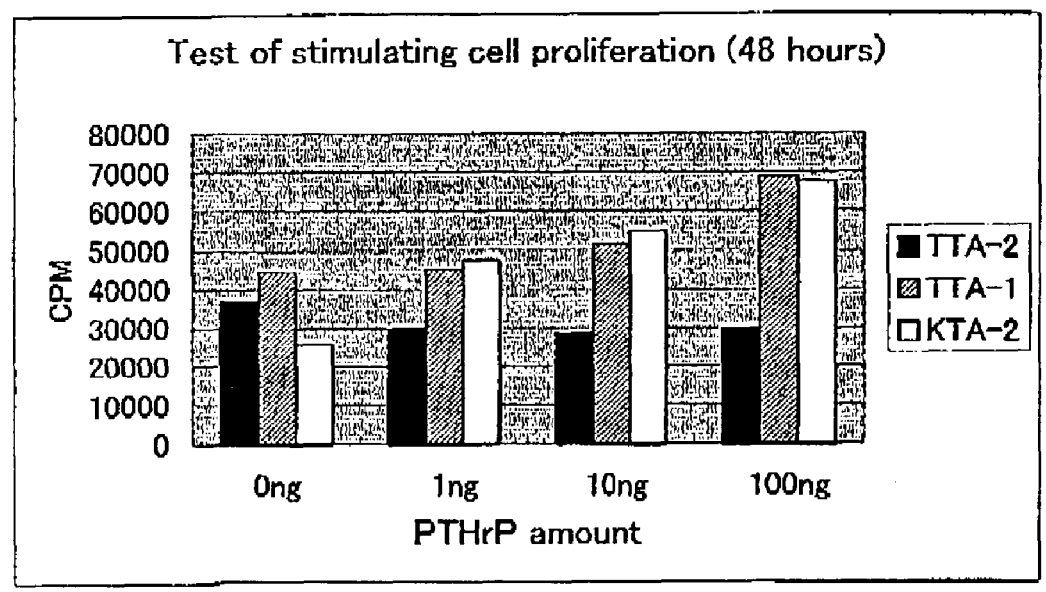

The purpose of the invention is to provide a proliferation inhibitor to cells whose proliferation is stimulated by a certain peptide site of a parathyroid hormone-related protein.

As a result of thorough studies to solve the above problems, the present inventors have completed the present invention by finding that addition of a PTHrP (34-53) fragment to cells expressing receptors for PTHrP(1-34) stimulates the proliferation of the cells; an anti-PTHrP (38-64) antibody inhibits proliferation of the cells stimulated with a PTHrP(34-53) fragment; and surprisingly, an anti-PTHrP(1-34) antibody also inhibits the cell proliferation.

Specifically, the present invention relates to a proliferation inhibitor for cells whose proliferation is stimulated by PTHrP (34-53), which comprises a substance inhibiting the binding of PTHrP (1-34) to its receptor. The present invention further relates to a therapeutic agent for diseases caused by cells whose proliferation is stimulated by PTHrP (34-53), which comprises a substance inhibiting the binding of PTHrP (1-34) to its receptor.

Here, the term "PTHrP (1-34)" means a peptide fragment consisting the sequence of amino acids 1 to 34 of the amino acid sequence of a parathyroid hormone related peptide. Further the term "PTHrP (34-53)" means a peptide fragment consisting the sequence of amino acids 34 to 53 of the amino acid sequence of a parathyroid hormone related peptide.

Moreover, the present invention relates to a proliferation inhibitor for cells whose proliferation is stimulated by PTHrP (34-53), which comprises a substance inhibiting the binding of PTHrP (34-53) to its receptor. The present invention further relates to a therapeutic agent for diseases caused by cells whose proliferation is stimulated by PTHrP (34-53), which comprises a substance inhibiting the binding of PTHrP (34-53) to its receptor.

Further, the present invention relates to a PTHrP production inhibitor, which comprises a substance inhibiting the binding of PTHrP (34-53) to its receptor.

Examples of diseases caused by cells whose proliferation is stimulated by PTHrP (34-53) include cancer, cachexia, arthrorheumatism, bone metastasis, labor pains, febris septica, compression of nerve and osteoporosis.

A substance which inhibits the binding of PTHrP (1-34) to its receptor is, for example, an anti-PTHrP (1-34) antibody or a PTHrP (7-34). The term "PTHrP (7-34)" means a peptide fragment that is a partial sequence of PTHrP (1-34) which contains deletion of amino acids 1 to 6 of PTHrP (1-34).

An example of a substance which inhibits the binding of PTHrP (34-53) to its receptor is an anti-PTHrP (38-64) antibody, anti-PTHrP (34-53) antibody, or the like. The term "PTHrP (38-64)" means a peptide fragment consisting the sequence of amino acids 38 to 64 of the amino acid sequence of a parathyroid hormone related peptide.

Any antibody can be used in the present invention, such as a monoclonal antibody and a polyclonal antibody. A preferred antibody is a monoclonal antibody. In addition, as a monoclonal antibody, a human antibody, a chimeric antibody or a humanized antibody is preferable.

The present invention also relates to a novel cell line which has a receptor for PTHrP(1-34) and whose proliferation is stimulated by PTHrP(34-53). A preferred novel cell line of the present invention is a cell line which normally produces no PTHrP substantially. The term "normally" means a condition wherein no PTHrP is present extracellularly. The term "produces no PTHrP substantially" means that the production amount of PTHrP is below the detection limit, for example, the production amount at a concentration below 0.01 pM/L.

The present invention further relates to a method for screening a substance inhibiting or promoting cell proliferation, which comprises adding a test substance into a medium containing the above cell line for culturing, and screening based on the culture result a substance capable of inhibiting or promoting proliferation of the cell line as an inhibitor or a promoter for cell proliferation.

Further, the present invention provides a method for cloning a gene of a cell surface molecule capable of binding to PTHrP (34-53), which comprises introducing an expression vector with cDNA derived from the above cell line incorporated therein into a host, culturing the obtained transformed host in a medium for the cell to express the cell surface molecule, adding labeled PTHrP(34-53) to the above medium for reaction with the above host, and isolating a gene encoding the cell surface molecule from positive host clones. When the above gene is expressed, a cell surface molecule (a protein expressed on the surface of a cell) which is expressed on the cell surface of the cell line of the present invention and is capable of binding to PTHrP(34-53) can be obtained.

This specification includes part or all of the contents as disclosed in the specifications and/or drawings or Japanese Patent Application Nos. 2000-131793 and 2000-173 834, which are priority documents of the present application.

The present invention provides a proliferation inhibitor for inhibiting proliferation of cells whose proliferation is stimulated by a peptide site, using a substance (e.g., anti-PTHrP (38-64) antibody) which inhibits biological activity of the peptide site corresponding to the sequence of amino acids 34 to 53 (PTHrP(34-53)) among the entire amino acid sequence (SEQ ID NO.: 1, 2 or 3) of a parathyroid hormone related peptide (PTHrP). There are three known types of PTHrP comprising 139, 141 and 173 amino acids, respectively, based on selective gene splicing. The amino acid sequences of the three types of PTHrPs are identical from the amino acid at position 1 to that at position 139. The amino acid sequence consisting of 139 amino acids, the sequence of 141 amino acids, and the sequence of 173 amino acids are shown in SEQ ID NO: 1, SEQ ID NO: 2, and SEQ ID NO: 3, respectively.

Moreover, the present invention provides a finding that an anti-PTHrP(1-34) antibody inhibits proliferation of cells whose proliferation is stimulated by PTHrP(34-53) peptide fragments. Specifically, it has been revealed that the anti-PTHrP(1-34) antibody, which is an antibody binding to a peptide consisting of the sequence of amino acids 1 to 34 of the entire amino acid sequence of PTHrP, can inhibit, without directly binding to a PTHrP(34-53) peptide fragment, the proliferation of cells whose proliferation is stimulated by the peptide fragment. Hence, a substance (e.g., anti-PTHrP(1-34) antibodies) inhibiting the binding of PTHrP(1-34) to its receptor is also effective as a proliferation inhibitor for inhibiting proliferation of cells whose proliferation is stimulated by the PTHrP(34-53) peptide fragment.

It is suggested by the present invention that the PTHrP(34-53) peptide fragment does not stimulate cell proliferation directly, but promotes the production of PTHrP itself through a cell surface molecule (e.g., receptors), and the produced PTHrP stimulates cell proliferation through the receptor for PTHrP(1-34).

The present invention will now be described in further detail.

1. Establishment of Cell Line

The novel cell line which has a receptor for PTHrP(1-34) and whose proliferation is stimulated by PTHrP(34-53) of the present invention can be established, for example, by the following method.

(1) Preparation of Cells for Culturing

Tumor cells excised from patients with anaplastic thyroid carcinoma are fragmented using scissors for autopsy. Here, the excised cells may be fragmented after transplantation into nude mice for proliferation.

(2) Culturing

The obtained cells are cultured under normal conditions. For example, the cells are cultured in an RPMI-1640 or Eagle's MEM medium supplemented with 10% fetal calf serum, glutamine, antibiotics and the like, for 2 to 3 weeks at 37° C. The proliferated cells are sub-cultured by treating with trypsin, EDEA or the like. The cell concentration is adjusted to 1 to 100 000 cells/ml. The cells are allowed to stand on a plate or a dish for culturing. As cells proliferate for 1 to 3 weeks after the start of culturing, the well size for the cells may be gradually scaled up. In addition, the cells may be transferred into a flask for culturing (e.g., 25 mm$^2$ and 75 mm$^2$).

The cells are sub-cultured by replacing with a new medium two to three times a week, or every 3 to 4 days.

(3) Determination of Established Cells

As described above, 6 types of thyroid cancer cell lines (TTA-1, TTA-2, KTA-1, KTA-2, KTA-3 and KTA-4) are obtained. These cells have the following characteristics.

(a) Character: Examination by an RT-PCR method for the presence or absence of receptors (referred to as PTHrPR) for PTHrP(1-34) revealed the presence of PTHrPR on the cell surfaces of 5 cell lines (TTA-1, KTA-1, KTA-2, KTA-3 and KTA-4).

(b) Functional characteristics:

[1] When 1×10$^5$ cells of each cell line were cultured for 2 days, PTHrPs at the following concentrations were produced.

| Cell line name | PTHrP concentration (pM/L) |
| --- | --- |
| TTA-1 | 0.01 |
| TTA-2 | 0.01 |
| KTA-1 | 7.76 |
| KTA-2 | 43.6 |
| KTA-3 | 24.4 |
| KTA-4 | 12.9 |

[2] Examination of cell proliferation ability with incorporation of $^3$H-thymidine ($^3$H-TdR) revealed that cells expressing PTHrPR proliferated in a PTHrP(34-53) fragment concentration-dependent manner. Further, addition of antibodies to the proliferated cells inhibited the proliferation.

Similarly to the above method, the cells of the present invention can be obtained by confirming the expression of PTHrPR and proliferation in a PTHrP(34-53) fragment concentration-dependent manner in known tissues expressing PTHrPR (bone, kidney, aorta, heart, brain, mammary gland, liver, spleen, lung, stomach, small intestine, adrenal gland, bladder, ovary, orchis, placenta, skin, skeletal muscle, and the like: Chohei SHIGENO; CLINICAL CALCIUM, 5(3), 79-83, 1995). Further, the cells of the present invention can also be obtained by allowing a known cell line to express PTHrPR by genetic engineering techniques, and confirming proliferation in a PTHrP(34-53) fragment concentration-dependent manner.

(4) Deposition of Cells

The above cell lines TTA-1, KTA-1, KTA-2 and KTA-3 were deposited at the International Patent Organism Depositary (IPOD), National Institute of Advanced Industrial Science and Technology, Japan (1-1, Higashi 1-chome, Tsukuba-shi, Ibaraki, Japan) as described below.

| Cell line name | Accession No. | Deposition date |
|---|---|---|
| TTA-1 | FERM BP-7523 | Jun. 08, 2000 |
| TTA-2 | FERM BP-7527 | Jun. 22, 2000 |
| KTA-1 | FERM BP-7524 | Jun. 08, 2000 |
| KTA-2 | FERM BP-7525 | Jun. 08, 2000 |
| KTA-3 | FERM BP-7526 | Jun. 08, 2000 |
| KTA-4 | FERM BP-7528 | Jun. 22, 2000 |

2. Preparation of PTHrP(34-53) Fragment

In the present invention, tumor cells prepared as described above are stimulated with PTHrP(34-53). The entire amino acid sequence (SEQ ID NO: 1, 2 or 3) of PTHrP is known. Thus, PTHrP(34-53) can be obtained by peptide synthesis, or a commercially available PTHrP(34-53) can be used.

When peptide synthesis is employed, PTHrP(34-53) can be obtained by normally employed chemical synthesis of peptide. Examples of a method for chemically synthesizing a peptide include an azide method, an acid chloride method, an acid anhydride method, a mixed acid anhydride method, a DCC method, an active ester method, a carbodiimidazole method and an oxidation-reduction method. In addition, either a solid phase or a liquid phase synthesis method may be applied for synthesis.

Specifically, amino acids that can form the peptide of the present invention are condensed, in case the products possess protecting groups by elimination of the protecting groups, band a target peptide can be synthesized. Any known method may be used for condensation and for elimination of protecting groups (Bodanszky, M. and Ondetti, M. A., Peptide Synthesis, Interscience Publishers, New York (1966); Schroeder and Luebke, The Peptide, Academic Press, New York (1965); Nobuo IZUMIYA et al., Basis and Experiment for Peptide Synthesis, Maruzen (1975); and the like).

After reaction, the target peptide is purified by a combination of normal purification methods, such as solvent extraction, distillation, column chromatography, liquid chromatography, and recrystallization. Whether or not the synthesized peptide is the target peptide can be analyzed by mass spectroscopy, nuclear magnetic resonance, electrophoresis, high performance liquid chromatography or the like.

3. Substance Inhibiting the Binding of PTHrP(1-34) to its Receptor

The term "a substance inhibiting the binding of PTHrP(1-34) to PTHrP(1-34) receptor" means either one or both of the following substances (a) and (b) (hereinafter also referred to as "PTHrP(1-34) inhibitor"):

(a) a substance inhibiting the binding of PTHrP(1-34) to PTHrP(1-34) receptor by binding with PTHrP(1-34), which is a ligand;

(b) a substance inhibiting the binding of PTHrP(1-34) to PTHrP(1-34) receptor by binding with PTHrP(1-34) receptor.

An example of the substance (a) above is an anti-PTHrP (1-34) antibody.

Examples of an anti-PTHrP(1-34) antibody include a humanized antibody, a human antibody (WO96/33735) or a chimeric antibody (Japanese Patent Application Laying-Open (kokai) No. 4-228089), as well as an antibody (#23-57-137-1 antibody) produced by a hybridoma #23-57-137-1. In addition, an antibody used herein may be either a polyclonal or a monoclonal antibody, and a monoclonal antibody is preferred.

An example of the substance (b) above is an antagonist (also referred to as "PTHrP(1-34) antagonist") for PTHrP(1-34) receptor. Examples of PTHrP(1-34) antagonist include, but are not limited thereto, a polypeptide and a low molecular weight substance. Specific examples of the antagonist include PTHrP(1-34) peptide containing substitution or deletion of at least one amino acid (for example, one or more amino acids), or a partial sequence of PTHrP(1-34) peptide (for example, PTHrP(7-34)). Further, examples of a substance which binds to PTHrP(1-34) receptor antagonistically with respect to PTHrP(1-34) include polypeptides having PTHrP(1-34) antagonist activity described in Japanese Patent Application Laying Open (kokai) No. 7-165790; Japanese Patent Application Laying-Open (kohyo) No. 5-509098; Peptides (UNITED STATES) 1995, 16 (6) 1031-1037; and Biochemistry (UNITED STATES) Apr. 28, 1992, 31 (16) 4026-4033. Furthermore, PTHrP(1-34) antagonists of the present invention also include, among the polypeptides illustrated above, a polypeptide containing deletion, substitution, addition or insertion of at least one (e.g., one or more) amino acid(s), and having equivalent PTHrP(1-34) antagonist activity.

4. Substance Inhibiting the Binding of PTHrP(34-53) to its Receptor

The term "a substance inhibiting the binding of PTHrP(34-53) to its receptor" of the present invention means either one or both of the following substances (a) and (b) (hereinafter also referred to as "PTHrP(34-53) inhibitor"):

(a) a substance inhibiting the binding of PTHrP(34-53) to PTHrP(34-53) receptor by binding with PTHrP(34-53), which is a ligand;

(b) a substance inhibiting the binding of PTHrP(34-53) to PTHrP(34-53) receptor by binding with PTHrP(34-53) receptor.

Examples of the above substance (a) include an anti-PTHrP(34-53) antibody and an anti-PTHrP(38-64) antibody. Examples of the above substance (b) include, but are not limited thereto, a polypeptide and a low molecular weight substance.

These PTHrP(34-53) inhibitors inhibit cell proliferation by inhibiting the binding of PTHrP(34-53) peptide site to its receptor expressed on the surface of a tumor cell.

5. Anti-PTHrP Antibody

The anti-PTHrP antibody (e.g., PTHrP (1-34) antibody, and anti-PTHrP (38-64) antibody) used in the present invention can be produced by any known method as a polyclonal or monoclonal antibody. Preferably, the above antibody used in the present invention is a monoclonal antibody derived from, particularly, a mammal. Examples of the mammal-derived monoclonal antibody include those produced by hybridomas and those produced by a genetic engineering technique from hosts transformed with expression vectors carrying a gene for the antibody.

(1) Monoclonal Antibody

A monoclonal antibody-producing hybridoma can be produced as follows. That is, PTHrP is used as an antigen for immunization in accordance with a conventional immunization method. The resulting immunocytes are fused to known parent cells by a conventional cell fusion method, and monoclonal antibody-producing cells are screened from the fused cells by a conventional screening method.

First, PTHrP (1-34) and PTHrP (38-64) which are partial fragments of a human PTHrP which is used as a sensitizing antigen for producing the antibody is chemically synthesized based on the PTHrP gene/amino acid sequence disclosed in Suva, L. J. et al., Science (1987) 237,893.

The mammal to be immunized with the sensitizing antigen is not particularly limited. However, the mammal is preferably selected taking into consideration of compatibility with the patent cell used for cell fusion. Generally, a rodent (e.g., mouse, rat, hamster), rabbit or monkey may be used.

The immunization of the mammal with the sensitizing antigen can be performed in accordance with any known method, for example, by injecting the sensitizing antigen to a mammal intraperitoneally or subcutaneously. More specifically, the sensitizing antigen is properly diluted with or suspended to phosphate-buffered saline (PBS) or physiological saline, the resulting dilution or suspension is then mixed with an appropriate amount of a conventional adjuvant (e.g., Freund's complete adjuvant) to give an emulsion. The emulsion is injected to a mammal several times at intervals of 4 to 21 days. For the immunization, the sensitizing antigen may be attached to a suitable carrier.

After the immunization, the serum antibody level is checked. When the serum antibody level is confirmed to reach a desired level, immunocytes are isolated from the mammal and then subjected to cell fusion. A preferable immunocyte is a spleen cell.

The parent cell used for the cell fusion (i.e., the counterpart of the cell fusion with the immunocyte) is a myeloma cell derived from a mammal. The myeloma cell is of any known cell line, and, for example, P3 (P3×63Ag8.653) (J. Immnol. (1979) 123, 1548-1550), P3×63Ag8U.1 (Current Topics in Microbiology and Immunology (1978) 81, 1-7), NS-1 (Kohler, G. and Milstein, C. Eur. J. Immunol. (1976) 6, 511-519), MPC-11 (Margulies, D. H. et al., Cell (1976) 8, 405-415); SP2/0 (Shulman, M. et al., Nature (1978) 276, 269-270), FO (de St. Groth, S. F. et al., J. Immunol Methods (1980) 35, 1-21), S194 (Trowbridge, I. S., J. Exp. Med. (1978) 148, 313-323) or R210 (Galfe, G. et al., Nature (1979) 277, 131-133).

Cell fusion of the immunocyte to the myeloma cell is basically performed in accordance with any known method, such as the method of Milstein et al. (Kohler, G. and Milstein, C., Methods Enzymol. (1981) 73, 3-46).

More specifically, the cell fusion is performed, for example, in a conventional nutrient culture medium in the presence of a cell fusion promoter. The cell fusion promoter may be polyethylene glycol (PEG) or a Sendai virus (hemagglutinating virus of Japan; HVJ). If desired, for the purpose of improving the fusion efficiency, an additive such as dimethyl sulfoxide may be incorporated.

The ratio between the immunocytes and the myeloma cells for the cell fusion may be any one. For example, the immunocytes are used in the amount 1-10 times larger than the myeloma cells. The culture medium used for the cell fusion is, for example, RPMI 1640 medium or MEM medium suitable for the growth of the above-mentioned myeloma cell lines, or other medium conventionally used for the culture of such cell lines. If desired, a serum supplement, such as feral calf serum (FCS), may be added to the culture medium.

The cell fusion is performed by fully mixing given amounts of the immmunocytes and the myeloma cells in the culture medium, adding a PEG solution (e.g., mean molecular weight: about 1000-6000) (which has been previously warmed to about 37° C.) to the mixture usually to a concentration of 30-60% (w/v), and then mixing the resulting solution, thereby producing the desired fusion cells (i.e., hybridomas). Subsequently, an appropriate culture medium is added to the culture solution successively, and centrifuged to remove the supernatant. This procedure is repeated several times to remove the cell fusion promoter or the like that are undesirable for the growth of the hybridomas, from the culture medium.

The obtained hybridomas can be selected by culturing in a conventional selective medium, such as hypoxanthine-aminopterin-thymidine (HAT) medium. The culturing of the hybridomas in HAT medium is performed for the time of period enough to cause the death of the cells other than the desired hybridomas (i.e., cells that fail to fuse), usually for several days to several weeks. Subsequently, conventional limiting dilution method is performed for screening and mono-cloning of the hybridomas that are secreting the desired antibody.

As a method other than preparing the hybridomas by immunizing a non-human mammal with the antigen as described above, a human lymphocyte may be sensitized with PTHrP in vitro, and then subjected the sensitized lymphocyte to cell fusion to a human-derived myeloma cell capable of infinite growth, thereby producing a human antibody having a binding activity against the PTHrP (Japanese Patent Publication No. 1-59878). Alternatively, a human antibody against PTHrP may be prepared by injecting PTHrP as an antigen to a transgenic animal that has the entire repertorics of human antibody genes to produce an anti-PTHrP antibody-producing cell, and then immortalizing the cells, thus producing the human antibody from the immortalized cell (International Patent Publication Nos. WO 94/25585, WO 93/12227, WO 92/03918 and WO 94/02602).

The monoclonal antibody-producing hybridoma prepared as above can be subcultured in a conventional culture medium and stored under liquid nitrogen for a long time of period.

For the production of a monoclonal antibody from the hybridoma, a method may be employed that involves culturing the hybridoma in accordance with a conventional technique and collecting the monoclonal antibody from the culture supernatant, or that involves injecting the hybridoma to a mammal compatible with the hybridoma to grow the hybridoma in the mammal and collecting the hybridoma from the ascites of the mammal. The former method is suitable for producing the antibody in high purity, while the latter method is suitable for producing the antibody in a large amount.

A specific example of such an antibody is #23-57-137-1 antibody (anti-PTHrP (1-34) antibody) or the like which is produced by a hybridoma clone #23-57-137-1.

The hybridoma clone #23-57-137-1 was designated as "mouse-mouse hybridoma #23-57-137-1" and deposited under the terms of the Budapest Treaty on Aug. 15, 1996 at the International Patent Organism Depositary (IPOD), National Institute of Advanced Industrial Science and Technology, Japan (1-1, Higashi 1-chome, Tsukuba-shi, Ibaraki, Japan) under the accession No. FERM BP-5631.

(2) Polyclonal Antibody

Antigens prepared as described above are administered to animals for immunization. A dosage of antigens per animal is 0.001 to 1000 µg when the animal is a rabbit and adjuvants are used.

For immunization, antigens are administered to mammals. Immunization is principally conducted by intravenous, intracutanous, subcutaneous, or intraperitoneal injection. Intervals of immunization are not specifically limited. Immunization is carried out for 3 to 10 times, preferably 3 to 4 times, at intervals of from a few days to a few weeks, preferably 2 to 3 week-intervals. Three to 10 days after the final immunization, antibody titer is measured. On a day that the maximum antibody titer is shown, blood is collected to obtain anti-serum. Antibody titers can be measured by ELISA (enzyme-linked immunosorbent assay), RIA (radioimmuno assay) or the like.

When purification of antibodies from anti-sera is necessary, antibodies can be purified by appropriately selecting one of, or in combination of known methods including an ammonium sulfate salting-out method, ion exchange chromatography, gel filtration and affinity chromatography.

(3) Recombinant Antibody

In the present invention, a recombinant-type monoclonal antibody may be used, which can be produced by cloning an antibody gene from the hybridoma, integrating the antibody gene into a suitable vector, introducing the vector into a host, and then producing the antibody from the host according to a conventional genetic recombination technique (see, for example, Vandamme, A. M. et al., Eur. J. Biochem. (1990) 192, 767-775, 1990).

Specifically, mRNA encoding variable (V) region of an anti-PTHrP antibody is isolated from the anti-PTHrP antibody-producing hybridoma. The isolation of the mRNA is performed by preparing a total RNA by any known method, such as guanidium ultracentrifugation method (Chirgwin, J. M. et al., Biochemistry (1979) 18, 5294-5299) and AGPC method (Chomezynski, P. et al., Anal. Biochem. (1987) 162, 156-159), and then producing the desired mRNA from the total RNA using mRNA Purification Kit (Pharmacia) or the like. Alternatively, the mRNA may also be prepared directly using QuickPrep mRNA Purification Kit (Pharmacia).

Next, cDNA for the antibody V-region is synthesized from the obtained mRNA with a reverse transcriptase. The synthesis of the cDNA is performed using AMV Reverse Transcriptase First-strand cDNA Synthesis Kit (Seikagaku Corporation) or the like. The cDNA may also be synthesized and amplified by 5'-RACE method (Frohman, M. A, et al., Proc. Natl. Acad. Sci. USA (1988) 85, 8998-9002; Belyavsky, A. et al., Nucleic Acids Res. (1989) 17, 2919-2932) using 5'-Ampli FINDER RACE Kit (CLONETECH) in combination with PCR method, or the like.

A DNA fragment of interest is isolated and purified from the resulting PCR product and then ligated to a vector DNA to obtain a recombinant vector. The recombinant vector is introduced into a host such as *E. coli*, and a colony containing a desired recombinant vector is selected. The nucleotide sequence of the DNA of interest in the recombinant vector is confirmed by, for example, dideoxynucleotide chain termination method.

Once DNA encoding the anti-PTHrP antibody V-region is obtained, the DNA is integrated into an expression vector containing a DNA encoding a desired antibody constant (C) region.

For the production of the anti-PTHrP antibody used in the present invention, the antibody gene is integrated into an expression vector so that the antibody gene can be expressed under the control of expression control regions (e.g., enhancer, promoter). A host cell is transformed with the expression vector to express the antibody.

In the expression of the antibody gene, a DNA encoding heavy (H) chain and a DNA encoding light (L) chain of the antibody may be integrated into separate expression vectors, and then a host cell is co-transformed with the resulting recombinant expression vectors. Alternatively, both the DNA encoding H-chain and the DNA encoding L-chain of the antibody may be integrated together into a single expression vector, and then a host cell may be transformed with the resulting recombinant expression vector (WO 94/11523).

For the production of the recombinant antibody, besides the above-mentioned host cells, a transgenic animal may also be used as a host. For example, the antibody gene is inserted into a predetermined site of a gene encoding a protein inherently produced in the milk of an animal (e.g., goat β-casein) to obtain a fusion gene. A DNA fragment containing the antibody gene-introduced fusion gene is injected into an embryo of a goat, and the embryo is then introduced into a female goat. The female goat having the embryo therein bears a transgenic goat. The antibody of interest is secreted in the milk from the transgenic goat or a progeny thereof. For the purpose of increasing the amount of the antibody-containing milk from the transgenic goat, an appropriate hormone may be administered to the transgenic goat (Ebert, K. M. et al., Bio/Technology (1994) 12, 699-702).

Further, a transgenic plant, such as Tobacco plant, may also be used instead of a transgenic animal.

(4) Modified Antibody

In the present invention, for the purpose of reducing the heterogenisity against a human body or the like, an artificially modified recombinant antibody may be used in addition to the above antibodies, such as a chimeric antibody, a humanized antibody, and a human antibody produced by transgenic mice or the like. These modified antibodies can be prepared by the following known methods.

A chimeric antibody usable in the present invention can be prepared by ligating the DNA encoding the antibody V-region prepared as set forth above to a DNA encoding a human antibody C-region, integrating the ligation product into an expression vector, and introducing the resulting recombinant expression vector into a host to produce the chimeric antibody.

A humanized antibody is also referred to as a "reshaped human antibody", in which the complementarity determining regions (CDRs) of an antibody of a non-human mammal (e.g., a mouse) are grafted to those of a human antibody. The general genetic recombination procedures for producing such humanized antibody are also known (EP 125023; WO 96/02576).

Specifically, a DNA sequence in which mouse antibody CDRs are ligated through framework regions (FRs) of a human antibody is amplified by PCR method using several oligonucleotides as primers which have been designed to have regions overlapping to the terminal regions of the CDRs and the FRs. The resulting DNA is ligated to a DNA encoding a human antibody C-region, and the ligation product is integrated into an expression vector. The resulting recombinant expression vector is introduced into a host, thereby producing the humanized antibody (EP 239044, WO 96/02576).

The FRs of the human antibody ligated through the CDRs are selected so that the CDRs can form a suitable antigen binding site. If necessary, an amino acid(s) in the FRs of the antibody V-region may be replaced so that the CDRs of the reshaped human antibody can form a suitable antigen binding site (Sato, K. et al., Cancer Res. (1993) 53, 851-856).

The C-region of the chimeric or humanized antibody may be any human antibody C-region, such as Cγ1, Cγ2, Cγ3 or Cγ4 for the H-chain, and Cκ or Cλ for the L-chain. The human antibody C-region may be modified for the purpose of improving the stable production of the antibody.

The chimeric antibody is composed of V-regions derived from a non-human mammalian antibody and C-regions derived from a human antibody. The humanized antibody is composed of CDRs derived from a non-human mammalian antibody and FRs and C-regions derived from a human antibody. The humanized antibody is useful as an active ingredient for the drug of the present invention, because the antigenicity of the antibody against a human body is reduced.

A specific example of the humanized antibody usable in the present invention is humanized #23-57-137-1 antibody; in which the CDRs are derived from mouse-derived #23-57-137-1 antibody; the L-chain is composed of the CDRs ligated through three FRs (FR1, FR2 and FR3) derived from human antibody HSU 03868 (GEN-BANK, Deftos, M. et al., Scand. J. Immunol., 39, 95-103, 1994) and a FR (FR4) derived from human antibody S25755 (NBRF-PDB); and the H-chain is composed of the CDRs ligated through FRs derived from human antibody S31679 (NBRF-PDB, Cuisinier, A. M. et al., Eur. J. Immunol. 23, 110-118, 1993) in which a part of the amino acid residues in the FRs is replaced so that the reshaped humanized antibody can exhibit an antigen-binding activity.

The *E. coli* strains containing the plasmids having DNAs encoding the H-chain and the L-chain of the humanized #23-57-137-1 antibody, respectively, are designated *Escherichia coli* JM109 (hMBC1HcDNA/pUC19) (for H-chain) and *Escherichia coli* JM109 (hMBC1Lqλ/pUC19) (for L-chain), respectively. These strains have been deposited under the terms of the Budapest Treaty on Aug. 15, 1996 at the National Institute of Bioscience and Human-technology, Agency of Industrial Science and Technology, Japan (1-3, Higashi 1-chome, Tsukuba-shi, Ibaraki, Japan), under the accession No. FERM BP-5629 for *Escherichia coli* JM109 (bMBC1HcDNA/pUC19), and under the accession No. FERM BP-5630 for *Escherichia coli* JM109 (hMBC1Lqλ/pUC19).

Further, a human antibody which is produced using transgenic mice or the like can also be used as the antibody of the present invention (Japanese Patent Application Laying-Open (Kokai) No. 2000-80100).

(5) Antibody Variants

The antibody used in the present invention may be a fragment thereof or a modified form of the above fragments (1) to (4). For example, the fragment of the antibody includes Fab, $F(ab')_2$, Fv, or a single chain Fv (scFv) composed of a H-chain Fv fragment and a L-chain Fv fragment linked together through a suitable linker. Specifically, such antibody fragments can be produced by cleaving the antibody with an enzyme (e.g., papain, pepsin) into antibody fragments, or by constructing a gene encoding the antibody fragment and inserting the gene into an expression vector and introducing the resulting recombinant expression vector into a suitable host cell, thereby expressing the antibody fragment (see, for example, Co, M. S., et al., J. Immunol. (1994), 152, 2968-2976; Better, M. & Horwitz, A. H., Methods in Enzymology (1989), 178, 476-496, Academic Press, Inc.; Plueckthun, A. & Skerra, A., Methods in Enzymology (1989) 178, 476-496, Academic Press, Inc.; Lamoyi, E., Methods in Enzymology (1989) 121, 652-663; Rousseaux, J. et al., Methods in Enzymology (1989) 121, 663-669; and Bird, R. E. et al., TIBTECH (1991) 9, 132-137).

The scFv can be produced by linking the H-chain V-region to the L-chain V-region through a linker, preferably a peptide linker (Huston, J. S. et al., Proc. Natl. Acad. Sci. USA (1988) 85, 5879-5883). The H-chain V-region and the L-chain V-region in the scFv may be derived from any one of the antibodies described herein. The peptide linker which binds the V-regions may be any single chain peptide, for example, of 12-19 amino acid residues.

The DNA encoding the scFv can be prepared by first amplifying a DNA encoding the H-chain V-region and a DNA encoding the L-chain V-region of the antibody separately using a DNA fragment encoding the entire region or a part of the H-chain that includes the V-region and a DNA fragment encoding the entire region or a part of the L-chain that includes the V-region as templates and primer pairs that define the terminal ends of the DNA fragments; and then amplifying a DNA encoding the peptide linker using a DNA fragment encoding the peptide linker as a template and a primer pair that define the terminal ends of the DNA fragment so that each terminal end of the peptide linker is ligated to the H-chain V-region and the L-chain V-region, respectively.

Once the DNA encoding the scFv is prepared, an expression vector carrying the DNA and a host transformed with the expression vector can be prepared by conventional methods. The scFv can be produced from the transformed host by a conventional method.

The fragments of the antibody may be produced by preparing genes for the fragments and expressing the genes in suitable hosts as described above. The antibody fragments is also encompassed in the "antibody" of the present invention.

As a modified form of the above-mentioned antibodies, for example, anti-PTHrP antibody conjugated to any molecule (e.g., polyethylene glycol) may also be used. Such modified antibodies are also encompassed in the "antibody" of the present invention. The modified antibodies can be prepared by chemical modifications of the antibodies. The chemical modification techniques suitable for this purpose have already been established in the art.

(6) Expression and Production of Recombinant Antibody or Modified Antibody

The antibody gene constructed as described above can be produced and expressed by known methods. For the expression in a mammalian cell, a conventional useful promoter, the antibody gene to be expressed and a poly(A) signal (located downstream to the 3' end of the antibody gene) are operably linked. For example, as the useful promoter/enhancer system, a human cytomegalovirus immediate early promoter/enhancer system may be used.

Other promoter/enhancer systems usable in the expression of the antibody used in the present invention include those derived from viruses (e.g., retrovirus, polyoma virus, adenovirus and simian virus 40 (SV40)) and those derived from mammalian cells (e.g., human elongation factor 1 α (HEF1 α).

When SV40 promoter/enhancer system is used, the gene expression may be performed readily by the method of Mulligan et al. (Nature (1979) 277, 108). When HEF1 α promoter/enhancer system is used, the gene expression may be preformed readily by the method of Mizushima et al. (Nucleic Acids Res. (1990) 18, 5322).

For the expression in *E. coli*, a conventional useful promoter, a signal sequence for secreting the antibody of interest and the antibody gene may be operably linked. As such a promoter, lacZ promoter or araB promoter may be used. When lacZ promoter is used, the gene expression may be performed by the method of Ward et al. (Nature (1098) 341, 544-546; FASBE J. (1992) 6, 2422-2427). When araB promoter is used, the gene expression may be performed by the method of Better et al. (Better et al., Science (1988) 240, 1041-1043).

Regarding the signal sequence for secretion of the antibody, when the antibody of interest is intended to be secreted in a periplasmic space of the *E. coli*, pelB signal sequence (Lei, S. P. et al., J. Bacteriol. (1987) 169, 4379) may be used. The antibody secreted into the periplasmic space is isolated and then refolded so that the antibody takes an appropriate configuration for use.

Regarding the replication origin, those derived from viruses (e.g., SV40, polyoma virus, adenovirus, bovine papilloma virus (BPV)) or the like may be used. In order to increase the gene copy number in the host cell system, the expression vector may further contain a selective marker gene, such as an aminioglycoside phosphotransferase (APH) gene, a thymidine kinase (TK) gene, an *E. coli* xanthine-guanine phosphoribosyltransferase (Ecogpt) gene and a dihydrofolate reductase (dhfr) gene.

For the production of the antibody used in the present invention, any expression system such as eukaryotic and prokaryotic cell systems may be used. The eukaryotic cell includes established cell lines of animals (e.g., mammals, insects, molds and fungi, yeast). The prokaryotic cell includes bacterial cells such as *E. coli* cells.

It is preferable that the antibody used in the present invention be expressed in a mammalian cell, such as a CHO, COS, myeloma, BHK, Vero or HeLa cell.

Next, the transformed host cell is cultured in vitro or in vivo to produce the antibody of interest. The culturing of the host cell may be performed by any known method. The culture medium usable herein may be DMEM, MEM, RPMI 1640 or IMDM medium. The culture medium may contain a serum supplement, such as fetal calf serum (FCS).

(7) Isolation and Purification of Antibody

The antibody expressed and produced as described above may be isolated from the cells or the host animal body and purified to uniformity. The isolation and purification of the antibody used in the present invention may be performed on an affinity column. Examples of a protein A column include Hyper D, POROS and Sepharose F. F. (Pharmacia). The method is not particularly limited and other methods conventionally used for the isolation and purification of an antibody may also be employed. For example, various chromatographs using columns other than the above-mentioned affinity column, filtration, ultrafiltration, salting out and dialysis may be used singly or in combination to isolate and purify the antibody of interest (Antibodies A Laboratory Manual. Ed. Harlow, David Lane, Cold Spring Harbor Laboratory, 1988).

(8) Determination of the Activities of the Antibody

The determination of the antigen-binding activity (Antibodies A Laboratory Manual, Ed. Harlow, David Lane, Cold Spring Harbor Laboratory, 1988) or the inhibitory activity against a ligand receptor (Harada, A. et al., International Immunology (1993) 5, 681-690) of the antibody used in the present invention may be performed by any known methods.

The method for the determination of the antigen-binding activity of the anti-PTHrP antibody used in the present invention may be BIACORE method (analytical method using surface plasmon resonance), ELISA (enzyme-linked immunosorbent assay), EIA (enzyme immunoassay), RIA (radioimmunoassay) or a fluorescent antibody. For example, when enzyme immunoassay is employed, a sample solution containing the anti-PTHrP antibody (e.g., a culture supernatant of anti-PTHrP antibody-producing cells, or the anti-PTHrP antibody in a purified form) is-added to a plate on which PTHrP (1-34) is previously coated. A secondary antibody labeled with an enzyme (e.g., alkaline phosphatase) is further added to the plate. The plate is incubated and washed. A substrate for the enzyme (e.g., p-nitrophenylphosphoric acid) is added to the plate, and the absorbance of the solution in the plate is measured to evaluate the antigen-binding activity of the antibody.

To confirm the activity of the antibody used in the present invention, a neutralizing activity of the antibody (e.g., anti-PTHrP antibody) may be determined.

6. Therapeutic Agent for Disease Caused by Bells Whose Proliferation is Stimulated by PTHrP (34-53)

The term "disease caused by cells whose proliferation is stimulated by PTHrP (34-53)" in the present invention means diseases which are caused by cells whose proliferation is stimulated by the biological activity of a peptide site corresponding to the sequence of amino acids 34 to 53 of the entire amino acid sequence (SEQ ID NO: 1, 2 or 3) of a parathyroid hormone-related protein (hereinafter referred to as "PTHrP").

Examples of diseases caused by cells whose proliferation is stimulated by PTHrP(34-53) include cancer, cachexia, chronic rheumatism, osteoarthritis, bone metastasis, osteolysis, bone destruction, proliferation of cancer cells present in bone tissues, labor pains, febris septica, compression of nerve, bone fracture, gingivitis, alveolar pyorrhea, periodontal disease, systemic inflammatory response syndrome (SIRS) or osteoporosis. Further, examples of cancer caused by cells whose proliferation is stimulated by PTHrP (34-53) include, but are not limited thereto, carcinoma planocellulare, lung cancer, carcinoma oesophagi, cancer of the cervix uteri, cancer of the vulva, cancer of head, cancer of cervix region, cancer of skin, hypernephroma, cancer of stomach, cancer of liver, cancer of spleen, cancer of pharynx, cancer of the tongue, bladder cancer, ovarian cancer, testicular carcinoma, cancer of colon, cancer of rectum, urothelial carcinoma, leukemia, myeloma, breast carcinoma, lymphoma and cancer of thyroid. In addition, multiple onset of the above diseases and the disease complicated with other diseases are also included.

A therapeutic agent containing the anti-PTHrP (1-34) antibody or anti-PTHrP (38-64) antibody of the present invention as an active ingredient may be administered orally or parenterally, but preferably parenterally. Specifically, the agent may be administered to a body as a whole or regionally, taking any dosage form, such as a transpulmonary agent (e.g., an agent administered with the help of a device such as a nebulizer), a nasogastric agent, a transdermic agent (e.g., ointment, cream) or an injection. Examples of an injection include an intravenous injection such as a drip, an intramuscular injection, an intraperitoneal injection and a subcutaneous injection. The route of administration may be properly selected depending on the age of a patient and the condition of a disease. An effective single dose may be selected within the range from 0.001 to 1,000 mg per kg of body weight. Alternatively, the dose to a patient may be selected from the range of 0.01 to 100,000 mg/body. However, the dose of the above agent is not particularly limited to these ranges.

The therapeutic agent of the present invention may be administered to a patient at any stage, including before or after the development of the above diseases or symptoms.

The therapeutic agent of the present invention may be formulated by any conventional method (Remington's Pharmaceutical Science, latest edition, Mark Publishing Company, Easton, USA). The preparation may further comprise pharmaceutically acceptable carriers and additives.

Examples of such carriers and additives include water, pharmaceutically acceptable organic solvents, amino acids, collagen, polyvinyl alcohol, polyvinylpyrrolidone, carboxyvinyl polymer, sodium carboxymethyl cellulose, sodium polyacrylate, alginate sodium, water soluble dextran, carboxymethyl starch sodium, pectin, methylcellulose, ethylcellulose, xanthan gum, gum Arabic, casein, agar, polyethylene glycol, diglycerine, glycerine, propylene glycol, Vaseline, paraffin, stearyl alcohol, stearic acid, human serum albumin (HSA), mannitol, sorbitol, lactose, and surfactants acceptable as pharmaceutical additives.

In the practical use, the additive is properly selected from the above members either singly or in combination depending on (without limitation) the dosage form employed. For example, for use as an injectable form, the anti-PTHrP antibody of the purified form is dissolved in a solvent (e.g., physiological saline, a buffer, a grape sugar solution) and then an adsorption-preventing agent (e.g., Polysorbate 80, Polysorbate 20, a gelatin, human serum albumin) is added thereto. The therapeutic agent of the present invention may also be in a re-constitutable freeze-dried form, which is dissolved before use. For the formulation of the freeze-dried dosage form, an excipient such as a sugar alcohol (e.g., mannitol, grape sugar) or a sugar may be incorporated.

7. Method for Screening Cell Proliferation Inhibitor

In the present invention, whether or not a test substance produces an inhibitory or promotion effect on cell proliferation can be determined based on proliferation of a target cell line. For example, the test substance to be screened is cultured with the cell line established as described above, instead of anti-PTHrP(1-34) or anti-PTHrP(38-64), as described below in Example.

8. Method for Screening Promoter or Inhibitor of PTHrP Production

In the present invention, whether a test substance can be used as a promoter or a inhibitor for PTHrP production can be determined based on the amount of PTHrP in a culture product resulting from culturing of the test substance to be screened with the cell line established as described above. Here, the term "culture product" means a culture supernatant, and either cultured cells or disrupted products thereof.

9. Cloning of Gene Encoding Cell Surface Molecule

In the present invention, a cell surface molecule of the cell line established as described above can be isolated by so-called expression cloning. The term "cell surface molecule" means a molecule which is involved in cell proliferation by transferring extracellular information (proteins, inorganic substances, various low molecular weight substances) into the cell, for example, a protein which functions as a receptor for PTHrP(34-53). Further, the term "expression cloning" means a method for cloning a gene using as an index the function exhibited by the target gene after expression. This method does not require information such as the nucleotide sequence of a gene or the amino acid sequence of a gene product. Furthermore, the method is preferable for cloning a gene with low expression amount.

In the present invention, an expression vector is prepared by incorporating cDNA derived from the above cell line therein, and the vector is introduced into an appropriate host, thereby preparing a transformant. The obtained transformed host is cultured, so that a cell surface molecule that cDNA encodes can be expressed. Normally, plate culturing is performed, colonies that appeared on the plate are transferred to a membrane through contact, and then ligands previously labeled with appropriate labels (PTHrP(34-53) in the invention) are added to the membrane for reaction. Next, positive host clones are selected based on signals of the labels and then genes encoding cell surface molecules are isolated from the obtained clones.

First, the cells established as described above are cultured, the cells are collected when the cells reach an appropriate density, and then mRNA is purified. mRNA can be purified by any known method. For example, after total RNA is obtained by treating the above established cells with a guanidine reagent, phenol reagent or the like, poly(A+)RNA(mRNA) is obtained by an affinity column method which uses poly U-sepharose or the like, using as a carrier oligo dT-cellulose or sepharose 2B, or by a batch method. Subsequently, a single-stranded cDNA is synthesized using the obtained mRNA as a template, an oligo dT primer and reverse transcriptase, and then a double-stranded cDNA is synthesized from the single-stranded cDNA. The thus obtained double stranded cDNA is incorporated into an appropriate expression vector to prepare a recombinant vector, thereby obtaining a cDNA library.

Examples of expression vectors used herein include plasmid vectors and phage vectors. Examples of a plasmid vector include a plasmid derived from *Escherichia coli* (for example, pBR322, pBR325, pUC118, pUC119, pBluescript II SK+/− and the like), a plasmid derived from *Bacillus subtilis* (for example, pUB110, pTP5 and the like), a plasmid derived from yeast (for example, YEp13, YEp24, YCp50 and the like). Examples of phage DNA include λ phage (λgt10, λgt11, M13mp18, M13mp19 and the like). Further, examples of other vectors that may be used include animal viruses, such as retrovirus, adenovirus and vaccinia virus, and insect virus vectors, such as baculovitus. Furthermore, a fusion plasmid with GST, GFP, His-tag, Myc-tag or the like bound thereto can be used.

The gene encoding a cell surface molecule must be incorporated into a vector so as to exhibit its function. In addition to a promoter and the gene of this invention, a cis element, such as an enhancer, a splicing signal, a poly A addition signal, a selection marker, or a ribosome binding sequence can also be integrated to the expression vector, if necessary. Further, as an expression inducer, isopropyl-β-D-thiogalactoside (IPTG) is used. Examples of selection markers include a dihydrofolic acid reducing enzyme gene, an ampicillin-resistant gene, and a neomycin-resistant gene.

Hosts for constructing cDNA libraries are not specifically limited so far as they can express the cell surface molecule gene. Examples of the host cells that can be used herein include bacteria belonging to the genera Escherichia, such as *Escherichia coli*; the genera Bacillus, such as *Bacillus subtilis*; and the genera Pseudomonas, such as *Pseudomonas putida*; yeasts such as *Saccharomyces cerevisiae* and *Schizosaccharomyces pombe*; animal cells, such as COS and CHO cells; and insect cells, such as Sf9 and Sf21.

When a bacterium such as *Escherichia coli* is used as a host cell, a preferable recombinant vector of the present invention can autonomously replicate in the bacterium and comprises a promoter, a ribosome binding sequence, the gene of this invention, and a transcription termination sequence. The recombinant vector may also contain a gene to regulate a promoter. Any promoter that can be expressed in a host cell, such as *Escherichia coli*, may be used. Examples of such a promoter include promoters derived from *Escherichia coli* or phages, such as trp promoters, lac promoters, $P_L$ promoters, and $P_R$ promoters. Artificially designed and modified promoters, such as tac promoters, may also be used. Any method to introduce recombinant vectors into bacteria, that is, to introduce DNA into bacteria, may be used and the method is not specifically limited. Examples of such methods include a method using calcium ion (Cohen, S. N. et al., Proc. Natl. Acad. Sci., USA, 69, 2110-2114 (1972)), an electroporation method (Becker, D. M. et al., Methods. Enzymol., 194, 182-187(1990)) and the like.

When yeast is used as a host cell, promoters are not specifically limited so far as they can be expressed in yeast. Examples of such a promoter include gal 1 promoters, gal 10 promoters, heat shock protein promoters, MFα1 promoters, PH05 promoters, PGK promoters, GAP promoters, ADH promoters, and AOX1 promoters. Methods to introduce recombinant vectors into yeast are not specifically limited, and any method for introducing DNA into yeast may be used. Examples of such methods include an electroporation method, a spheroplast method (Hinnen, A. et al., Proc. Natl.

Acad. Sci., USA, 75, 1929-1933, (1978)), a lithium acetate method (Itoh, H., J. Bacteriol., 153: 163-168, (1983)) and the like.

When an animal cell is used as a host cell, examples of a host cell include COS cells, Vero cells, Chinese hamster ovarian cells (CHO cells) and mouse myeloma cells. Examples of promoters include EF1α promoters, SRα promoters, SV40 promoters and LTR promoters. In addition, early gene promoters of human cytomegaloviruses may also be used. Examples of methods of introducing recombinant vectors into animal cells include electroporation, calcium phosphate transfection and lipofection.

When an insect cell is used as a host cell, Sf9 cells, Sf21 cells and the like are used. Examples of methods of introducing recombinant vectors into insect cells include calcium phosphate transfection, lipofection, and electroporation.

Next, the above transformed host cells are inoculated and cultured on appropriate media (e.g., solid plate media). Culturing can be performed under conditions which enable preferable expression of DNA libraries within host cells. Thus, for example, plaques are formed when phage vectors are used as expression vectors, and then expression of inserted genes results in production of protein in the plaques. An expression inducer is added when it is required for expression vectors to express incorporated genes. An expression inducer may be added previously and directly into culture solution, or impregnated to a membrane.

Subsequently, a membrane is brought into contact with the above plate surface, so as to transfer the produced protein onto the membrane. A preferred membrane used in the method of the invention is a membrane which is impregnated with an expression inducer and to which protein can be transferred. Normally employed blotting membranes, such as a nitrocellulose membrane or a nylon membrane can be used. To eliminate medium components, cells, and the like transferred from the plate, the membrane may be washed and then treated with a protein modifier. A cleaning agent is, for example, Tris-HCl buffer or the like. Examples of a protein modifier include guanidine hydrochloride, urea, and various reducing reagents. Then, the membrane is treated with a regenerant to regenerate protein on the membrane, washed, and then a solution containing labeled ligands is applied to the membrane. A ligand used in the present invention is PTHrP (34-53). Examples of a label that can be used herein include fluorescent labels, biotin labels, enzyme labels, antibody labels and the lice.

Accordingly, when host clones (positive clones) containing DNA encoding a ligand-binding protein are present on the above plate, labeled ligands will bind to corresponding proteins on the membrane. By detecting the label, positive clones on the plate can be determined.

Vectors are isolated from the thus obtained host clones according to standard techniques, thereby obtaining a target gene.

BEST MODE FOR CARRYING OUT THE INVENTION

Hereinafter, tile present invention will be described in greater detail with reference to the following Examples, which do not limit the technical scope of the invention.

EXAMPLE 1

Establishment of Anaplastic Thyroid Carcinoma Cell Line

Tumors excised from several patients with anaplastic thyroid carcinoma were fragmented using scissors for autopsy. Here, a part of the tumors was transplanted into nude mice to form tumors, and then the tumors were removed and fragmented.

The fragmented tumors were placed on culture plates supplemented with 10% fetal calf serum-containing RPMI1640 (Gibco) and cultured in a $CO_2$ incubator for 20 days. During culturing, media were exchanged at an interval of 3 to 7 days. After culturing, increased cells were treated with 0.25% trypsin and 0.02 mM EDTA, and then sub-cultured.

The cell lines obtained as described above are named TTA-1 and TTA-2 (both derived from tumors formed in nude mice), and KTA-1, KTA-2, KTA-3 and KTA-4.

EXAMPLE 2

Measurement of PTHrP Production Ability of Cell Lines and Expression of Receptors (1) PTHrP Production Ability TTA-1 and TTA-2, and KTA-1 and KTA-4 were treated with trypsin, and then the number of viable cells not stained with trypan blue was counted with a hemocytometer. Subsequently, $1 \times 10^5$ cells were inoculated on a 35 mm culture plate, and then cultured at 37° C. for 2 days. The obtained culture solution was collected, and then the PTHrP amount was measured using a PTHrP measurement kit (DAIICHI RADIO-ISOTOPE LABS., LTD.) according to the directions attached to the kit.

The results are as follows.

| Cell line name | PTHrP concentration (pM/L) |
| --- | --- |
| TTA-1 | 0.01 |
| TTA-2 | 0.01 |
| KTA-1 | 7.76 |
| KTA-2 | 43.6 |
| KTA-3 | 24.4 |
| KTA-4 | 12.9 |

Measurement of the PTHrP amount revealed that KTA-1, KTA-2, KTA-3 and KTA-4 produced PTHrP.

(2) Expression of Receptor

TTA-1 and TTA-2, and KTA-1 and KTA-4 were treated with trypsin, and then the number of viable cells not stained with trypan blue was counted with a hemocytometer. Subsequently, $1 \times 10^5$ cells were inoculated on a 35 mm culture plate, and then cultured at 37° C. for 2 days. The obtained cells were collected, and then mRNA was prepared using an mRNA preparation kit (Gibco BRL) according to the directions attached to the kit (TRIS01 reagent)

The mRNA obtained as described above was amplified using a RT-PCR kit (TOYOBO, RT-PCR High). The sequences of the primers are as follows.

```
Sense strand:
5'-GAAGCTGCTCAAATCGACG-3'      (SEQ ID No: 4)

Anti-sense strand:
5'-TTGATCTCAGCTTGACCTCG-3'     (SEQ ID NO: 5)
```

Using a reaction solution with the following composition, PCR was performed by reaction at 94° C. for 60 sec, followed by 40 cycles of reaction, each cycle consisting of 94° C. for 60 sec, 57° C. for 60 sec and 72° C. for 60 sec.

| | |
|---|---|
| cDNA (corresponding to RNA 1 μg/μl) | 0.5 μl |
| 10 × buffer | 1.8 μl |
| 2.5 mM dNTP | 1.0 μl |
| Sense primer (10 μM) | 0.5 μl |
| Anti-sense primer (10 μM) | 0.5 μl |
| Takara Ex Taq | 0.2 μl |
| H₂O | 15.5 μl |
| Total volume | 20 μl/sample |

After PCR, 3μl of the reaction solution was subjected to 2% agarose gel (1×TAE buffer) electrophoresis.

As a result, a 201 bp band was confirmed. A 308 bp band was confirmed for β-actin as a control.

EXAMPLE 3

PTHrP Stimulation Test

After treating TTA-1, TTA-2, and KTA-2 with trypsin, the number of viable cells not stained with trypan blue was counted with a hemocytometer. Subsequently, $1 \times 10^4$ cells were inoculated on a 96-well multi-plate (Falcon), and then cultured in a $CO_2$ incubator at 37° C. for 2 days. On day 2 after culturing, the culture solution was replaced by a serum-free medium, and then culturing was performed for 1 day. PTHrP (34-53) (Calbiochem) at concentrations of 0 (PTHrP-free), 1, 10 and 100 ng/mL were added, followed by treatment with trypsin 24 and 48 hours later.

The cells were labeled with $^3$H-TdR for 6 hours (0.25 μCi/well), collected, and then incorporation of $^3$H-TdR was measured using a liquid scintillation counter. Here, triplicate measurement was performed, and the mean value was obtained.

FIG. 1 shows the result. As shown in FIG. 1, with both trypsin treatment at 24 hours and at 48 hours after addition, TTA-1 and KTA-2 cell lines were confirmed to proliferate depending on the concentration of PTHrP.

EXAMPLE 4

Inhibition Test for Cell Proliferation

TTA-1, TTA-2, and KTA-2 were treated with trypsin, and then the number of viable cells not stained with trypan blue was counted with a hemocytometer. Subsequently, $1 \times 10^4$ cells were inoculated on a 96-well multi-plate (Falcon), and then cultured in a $CO_2$ incubator at 37° C. for 2 days. On day 2 after culturing, the culture solution was replaced by a serum-free medium, and then culturing was performed for 1 day. PTHrP(34-53) (Calbiochem) at concentrations of 0 (PTHrP-free), 1, 10 and 100 ng/mL were added, and then neutralization antibodies were added (anit-PTHrP(1-34) antibodies of CHUGAI PHARMACEUTICAL CO., LTD., and anti-PTHrP(38-64) antibodies of Oncogene). Each type of the antibodies at a concentration of 1 μg/ml was added simultaneously with PTHrP. At 24 and 48 hours after addition of antibodies, trypsin treatment was performed. Here, a test group not supplemented with the antibodies was a control group.

The cells were labeled with $^3$H-TdR for 6 hours (0.25 μCi/well), collected, and then incorporation of $^3$H-TdR was measured using a liquid scintillation counter.

Figure 2:
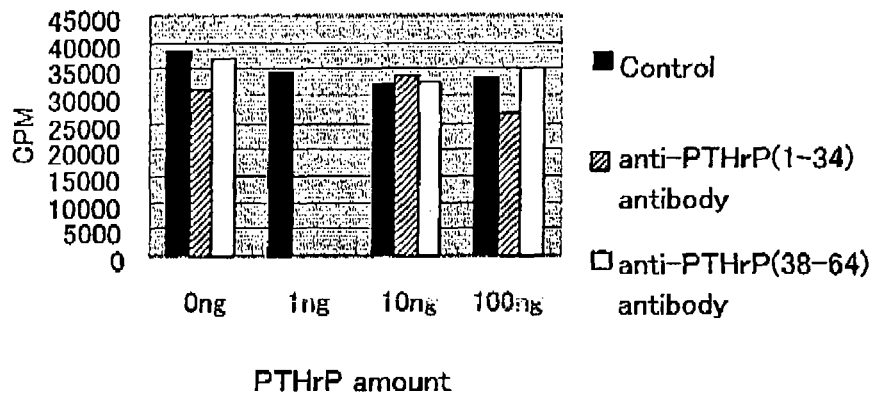
FIG. 2 shows the result of a test of inhibiting cell proliferation. Briefly, TTA-2 (top panel), TTA-1 (middle panel), and KTA-2 (bottom panel) cells were prepared as described above for FIG. 1. Cells were simultaneously treated with PTHrP (34-53) (as described above) and neutralizing antibodies at concentrations of 1 µg/mL (either anti-PTHrP (1-34) antibody (Chugai Pharmaceutical, hatched bars) or anti-PTHrP (38-64) antibody (Oncogene, unfilled bars)). Control cells (solid bars) were not treated with antibodies. At 24 hours after addition of antibodies, trypsin treatment was performed. Cells were labeled as described above for FIG. 1 and incorporation of label was measured by liquid scintillation counting.
Figure 2:
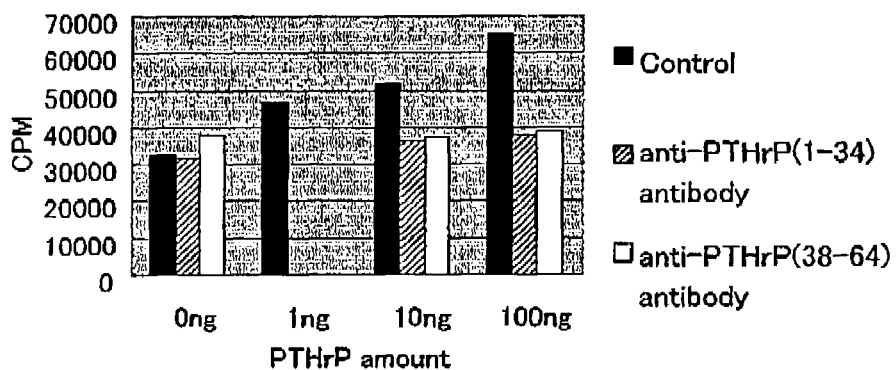
Figure 2:
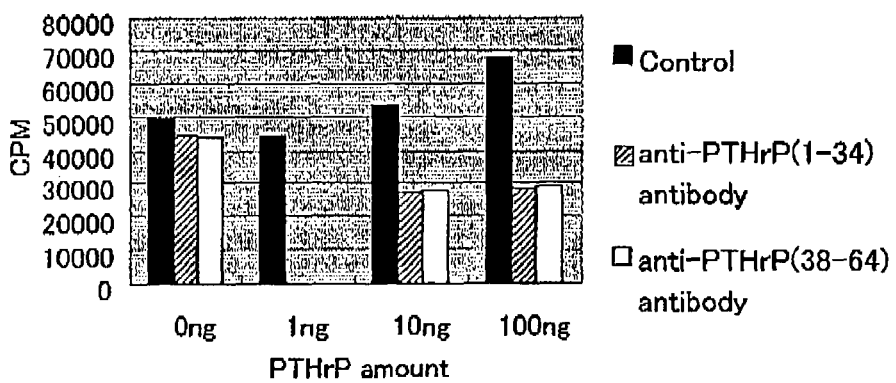
Figure 3:
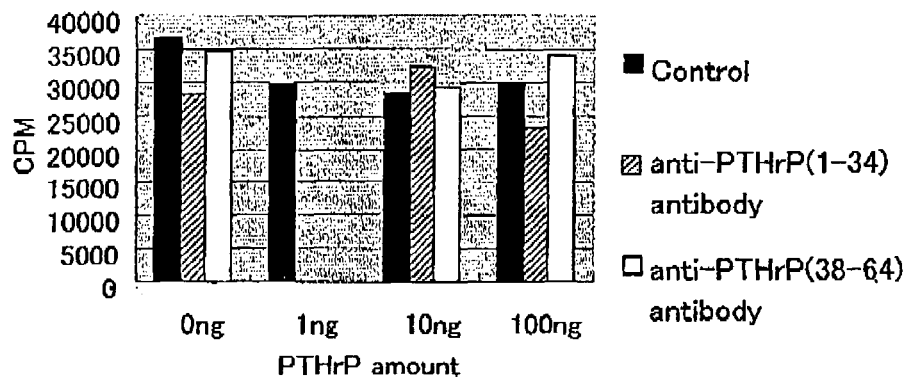
FIG. 3 shows the result of a test of inhibiting cell proliferation. Briefly, TTA-2 (top panel), TTA-2 (middle panel), and KTA-2 (bottom panel) cells were treated with PTHrP(34-53) and neutralizing antibodies (anti-PTHrP(1-34), hatched bars, or anti-PTHrP(38-64), unfilled bars), or were treated with PTHrP(34-53) only (control, solid bars), as described above for FIG. 2. At 48 hours after addition of antibodies, trypsin treatment was performed. Cells were labeled as described above for FIG. 1 and incorporation of label was measured by liquid scintillation counting.
Figure 3:
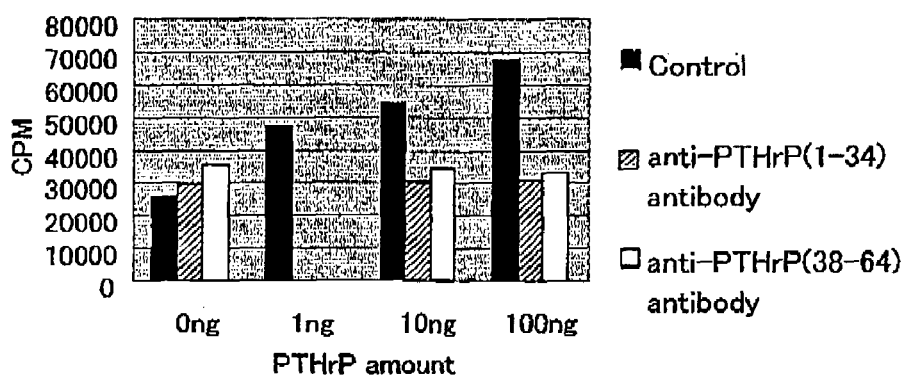
Figure 3:
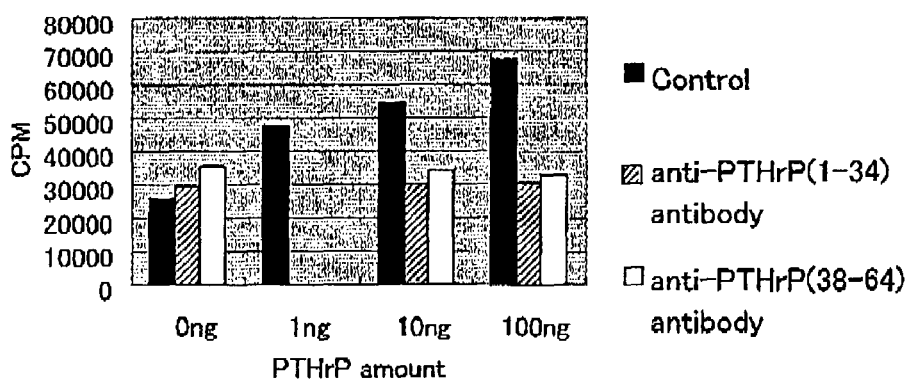

FIGS. 2 and 3 show the results. As shown in FIGS. 2 (trypsin treatment after 24 hours) and 3 (trypsin treatment after 48 hours), it was confirmed that with both trypsin treatments, anti-PTHrP antibodies significantly inhibited the proliferation of TTA-1 and KTA-2 cell lines regardless of the concentration of PTHrP.

All publications, patents and patent applications cited herein are incorporated herein by reference in their entirety.

Industrial Applicability

The present invention provides a cell proliferation inhibitor for cells whose proliferation is stimulated by a parathyroid hormone related peptide fragment. The proliferation inhibitor of the present invention is useful in treating diseases, such as cancer, which are induced by the cell proliferation.

Sequence Listing Free Text

SEQ ID NO: 4: Synthesized DNA
SEQ ID NO: 5: Synthesized DNA

The invention claimed is:

1. A method of inhibiting the proliferation of a thyroid carcinoma cell in vitro which express a PTH/PTHrP receptor and which is stimulated by PTHrP34-53 parathyroid hormone-related peptide fragment comprising:

contacting said cell with an amount of an antibody that binds to residues 1-34 of parathyroid hormone related peptide fragment.

2. The method of claim 1, wherein said antibody is a monoclonal antibody.

3. The method of claim 1, wherein said antibody is a chimeric antibody.

4. The method of claim 1, wherein said antibody is a humanized antibody.

5. The method of claim 1, wherein said antibody is humanized antibody #23-57-137-1.

* * * * *

```
SEQUENCE LISTING

<160> NUMBER OF SEQ ID NOS: 5

<210> SEQ ID NO 1
<211> LENGTH: 139
<212> TYPE: PRT
<213> ORGANISM: Homo sapiens

<400> SEQUENCE: 1

Ala Val Ser Glu His Gln Leu Leu His Asp Lys Gly Lys Ser Ile Gln
  1               5                  10                  15

Asp Leu Arg Arg Arg Phe Phe Leu His His Leu Ile Ala Glu Ile His
                 20                  25                  30

Thr Ala Glu Ile Arg Ala Thr Ser Glu Val Ser Pro Asn Ser Lys Pro
             35                  40                  45

Ser Pro Asn Thr Lys Asn His Pro Val Arg Phe Gly Ser Asp Asp Glu
         50                  55                  60

Gly Arg Tyr Leu Thr Gln Glu Thr Asn Lys Val Glu Thr Tyr Lys Glu
 65                  70                  75                  80
```

```
Gln Pro Leu Lys Thr Pro Gly Lys Lys Lys Gly Lys Pro Gly Lys
            85                  90                  95

Arg Lys Glu Gln Glu Lys Lys Lys Arg Arg Thr Arg Ser Ala Trp Leu
                100                 105                 110

Asp Ser Gly Val Thr Gly Ser Gly Leu Glu Gly Asp His Leu Ser Asp
            115                 120                 125

Thr Ser Thr Thr Ser Leu Glu Leu Asp Ser Arg
            130                 135

<210> SEQ ID NO 2
<211> LENGTH: 141
<212> TYPE: PRT
<213> ORGANISM: Homo sapiens

<400> SEQUENCE: 2

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
                20                  25                  30

Thr Ala Glu Ile Arg Ala Thr Ser Glu Val Ser Pro Asn Ser Lys Pro
            35                  40                  45

Ser Pro Asn Thr Lys Asn His Pro Val Arg Phe Gly Ser Asp Asp Glu
        50                  55                  60

Gly Arg Tyr Leu Thr Gln Glu Thr Asn Lys Val Glu Thr Tyr Lys Glu
 65                 70                  75                  80

Gln Pro Leu Lys Thr Pro Gly Lys Lys Lys Gly Lys Pro Gly Lys
            85                  90                  95

Arg Lys Glu Gln Glu Lys Lys Lys Arg Arg Thr Arg Ser Ala Trp Leu
                100                 105                 110

Asp Ser Gly Val Thr Gly Ser Gly Leu Glu Gly Asp His Leu Ser Asp
            115                 120                 125

Thr Ser Thr Thr Ser Leu Glu Leu Asp Ser Arg Arg His
            130                 135                 140

<210> SEQ ID NO 3
<211> LENGTH: 173
<212> TYPE: PRT
<213> ORGANISM: Homo sapiens

<400> SEQUENCE: 3

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
                20                  25                  30

Thr Ala Glu Ile Arg Ala Thr Ser Glu Val Ser Pro Asn Ser Lys Pro
            35                  40                  45

Ser Pro Asn Thr Lys Asn His Pro Val Arg Phe Gly Ser Asp Asp Glu
        50                  55                  60

Gly Arg Tyr Leu Thr Gln Glu Thr Asn Lys Val Glu Thr Tyr Lys Glu
 65                 70                  75                  80

Gln Pro Leu Lys Thr Pro Gly Lys Lys Lys Gly Lys Pro Gly Lys
            85                  90                  95

Arg Lys Glu Gln Glu Lys Lys Lys Arg Arg Thr Arg Ser Ala Trp Leu
                100                 105                 110

Asp Ser Gly Val Thr Gly Ser Gly Leu Glu Gly Asp His Leu Ser Asp
            115                 120                 125
```

```
Thr Ser Thr Thr Ser Leu Glu Leu Asp Ser Arg Thr Ala Leu Leu Trp
    130                 135                 140

Gly Leu Lys Lys Lys Lys Glu Asn Asn Arg Arg Thr His His Met Gln
145                 150                 155                 160

Leu Met Ile Ser Leu Phe Lys Ser Pro Leu Leu Leu Leu
                165                 170

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
gaagctgctc aaatccacg                                              19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
ttgatctcag cttgacctcg                                             20
```